(12) United States Patent
Maillere et al.

(10) Patent No.: US 10,550,166 B2
(45) Date of Patent: Feb. 4, 2020

(54) IMMUNOGENIC PEPTIDES OF THE CYCLIN B1 TUMOR ANTIGEN

(71) Applicant: Commissariat a l'Energie Atomique et aux Energies Alternatives, Paris (FR)

(72) Inventors: Bernard Maillere, Versailles (FR); Claire Chevaleyre, Paris (FR); Florence Castelli-Golfier, Chatillon (FR); Emmanuel Favry, Savigny sur Orge (FR); Anaïs M'Houmadi, Alfortville (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 15/701,863

(22) Filed: Sep. 12, 2017

(65) Prior Publication Data
US 2018/0086804 A1 Mar. 29, 2018

Related U.S. Application Data

(62) Division of application No. 14/902,721, filed as application No. PCT/IB2014/062863 on Jul. 4, 2014, now abandoned.

(30) Foreign Application Priority Data

Jul. 5, 2013 (FR) .................................... 13 56661

(51) Int. Cl.
*A61K 39/00* (2006.01)
*C07K 14/47* (2006.01)
*C07K 7/08* (2006.01)

(52) U.S. Cl.
CPC ...... *C07K 14/4738* (2013.01); *A61K 39/0011* (2013.01); *C07K 7/08* (2013.01); *A61K 39/00* (2013.01)

(58) Field of Classification Search
None
See application file for complete search history.

(56) References Cited

U.S. PATENT DOCUMENTS

2006/0147460 A1 7/2006 Finn et al.
2010/0291082 A1 11/2010 Zurawski et al.

FOREIGN PATENT DOCUMENTS

WO 03/033520 A2 4/2003
WO 2010/011994 A2 1/2010

OTHER PUBLICATIONS

International Search Report issued in corresponding International Patent Application No. PCT/IB2014/062863 dated Dec. 2, 2014.
Vella et al., "Healthy individuals have T-cell and antibody responses to the tumor antigen cyclin B1 that when elicited in mice protect from cancer," PNAS, 106: 14010-14015 (2009).
Sørensen et al., "CD8 T-cell Responses against Cyclin B1 in Breast Cancer Patients with Tumors Overexpressing p53," Clinical Cancer Research, 15: 1543-1549 (2009).
Suzuki et al., "T Cell-Dependent Antibody Responses against Aberrantly Expressed Cyclin B1 Protein in Patients with Cancer and Premalignant Disease," Clinical Cancer Research, 11: 1521-1526 (2005).
Kao et al., "Identification of Cyclin B1 as a Shared Human Epithelial Tumor-Associated Antigen Recognized by T Cells," Journal of Experimental Medicine, 194: 1313-1323 (2001).
Andersen et al., "Identification of a cyclin B1-derived CTL epitope eliciting spontaneous responses in both cancer patients and healthy donors," Cancer Immunology, Immunotherapy, 60: 227-234 (2011).
Klein-González et al., "Cyclins against cancer: a novel family of tumor antigens?" Immunotherapy, 2: 595-597 (2010).
"Helical protein secondary structure fragment, SEQ ID 7954," Database Geneseq EBI Accession No. GSP: AYK82740 (2010).
Graziano et al., "Characterization of T cell responses to cyclin B1 as a tumor antigen," FASEB Journal, 16: A668 (2002).
Kao et al., "Identification of Cyclin B1 as an Epithelial Tumor Antigen," FASEB Journal, 15: A1206 (2001).
Yu et al., "Aberrant cyclin B1 expression in human tumors and cell lines," FASEB Journal, 15: A1206 (2001).
Yu et al., "Immune recognition of cyclin B1 as a tumor antigen is a result of its overexpression in human tumors that is caused by non-functional p53," Molecular Immunology, 38: 981-987 (2001).
Registry (STN) [Oct. 31, 2015 (search date : Jan. 16, 2019], CAS Registration No. 611264 to 69-8 (online, 2003).

*Primary Examiner* — Daniel C Gamett
(74) *Attorney, Agent, or Firm* — Morgan, Lewis & Bockius LLP

(57) ABSTRACT

The present invention relates to peptides comprising at least one CD4+ T epitope, which is immunodominant in vitro, of the cyclin B1 tumor antigen, said peptides being capable of stimulating a specific human CD4+ T lymphocyte response in subjects who have varied HLA II molecules, and to the use of these peptides as a cancer vaccine and as a reagent for the diagnosis of cancer or the immunomonitoring of the cellular response against cyclin B1 during cancer or during an anticancer treatment.

16 Claims, 2 Drawing Sheets

Figure 1:
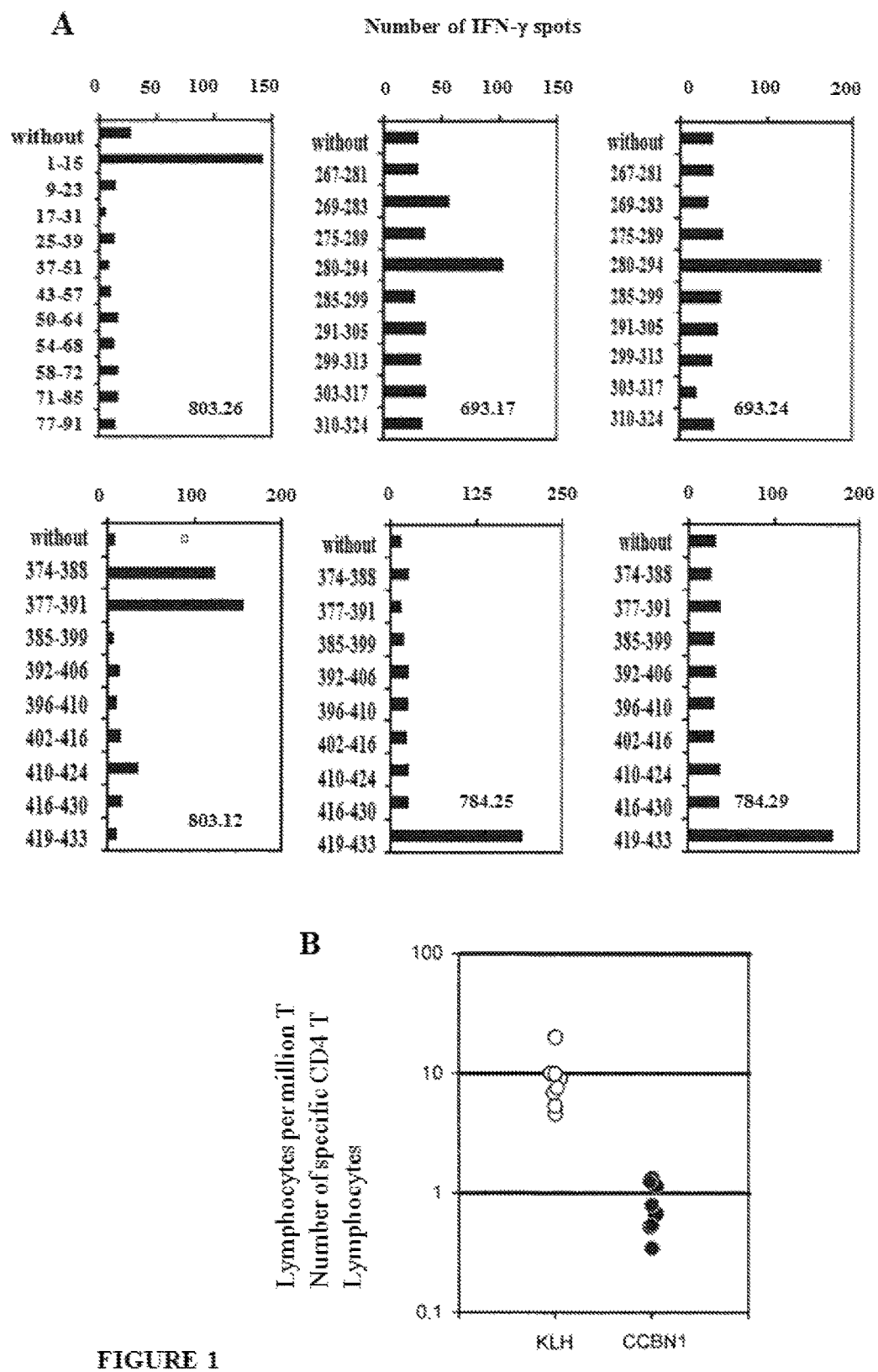

Specification includes a Sequence Listing.

IMMUNOGENIC PEPTIDES OF THE CYCLIN B1 TUMOR ANTIGEN

SEQUENCE LISTING SUBMISSION VIA EFS-WEB

A computer readable text file, entitled "SequenceListing.txt" created on or about 12 Sep. 2017, with a file size of about 31 kb contains the sequence listing for this application and is hereby incorporated by reference in its entirety.

The invention relates to immunogenic peptides derived from the cyclin B1 tumor antigen which are capable of binding to numerous class II HLA (HLA II) molecules and of inducing, in humans, a specific activation of CD4+ T lymphocytes in subjects who have varied HLA II molecules. The invention also relates to the use of such peptides as a cancer vaccine and as a reagent for the diagnosis of cancer or the immunomonitoring of the cellular response against cyclin B1 during cancer or during an anticancer treatment.

The differentiation of cells into tumor cells is the result of a genetic dysregulation which promotes proliferation thereof and expansion thereof in the organism. This dysregulation results in the expression of proteins that are normally sparingly expressed or not expressed in normal cells or expressed transiently. Among these proteins, some are expressed in sufficient amount to be recognized by the immune system and constitute tumor antigens. Antitumor vaccination uses these tumor antigens as a target in order to be able to induce a tumor-specific immune response which spares the healthy cells. These antigens are divided up into several categories, depending on their mode of expression.

Since the discovery of tumor-specific cytotoxic $CD8^+$ T lymphocytes (CTLs), a considerable effort has been made to induce the activation of these cells. Many studies relate to the location of the peptides that are recognized by $CD4^+$ T lymphocytes, given that it is now acknowledged that CTL induction is dependent on the activation of these cells (Assudani et al., Cancer Immunol. Immunother., 2007, 56, 70-80), that $CD4^+$ T lymphocytes exercise a control of the tumors via CTL-independent mechanisms, probably via macrophage activation, and that they may also be cytotoxic. $CD4^+$ T lymphocytes recognize tumor peptides (known as $CD4^+$ T epitopes) presented to them by the class II HLA molecules. The recognition can take place directly (i.e. the tumor itself presents these peptides to the T lymphocytes), but it is also likely that the main activation pathway involves dendritic cells. These cells, which possess a high number of class II HLA molecules at their surface and are capable of capturing tumor cell debris, are in fact the main antigen-presenting cells capable of recruiting naive T lymphocytes in vivo.

There are three types of class II HLA molecules: HLA-DR, HLA-DQ and HLA-DP. The HLA-DR molecule encoded by the DRB1 gene is the most widely expressed and the most widely studied. It appears to participate mostly in the response of $CD4^+$ T lymphocytes which are in fact usually HLA-DRB1-restricted. Many individuals possess other loci encoding HLA-DR molecules and called DRB3, DRB4 and DRB5. There are many HLA II molecule variants. Thus, 1285 different HLA-DRB1 alleles, encoding 959 different proteins, are present throughout the world. However, the alleles are not uniformly distributed throughout the world. For example, in Europe and in the USA, 7 HLA-DR molecules encoded by HLA-DRB1 (HLA-DRB1*01:01, 15:01, 03:01, 04:01, 11:01, 13:01, 07:01), the HLA-DRB3*01:01, -DRB4*01:01 and -DRB5*01:01 alleles and the HLA-DP4 molecules encoded by the (DPB1*0401 and DPB1*0402) alleles are predominant and cover most of the population (Table I).

TABLE I

Phenotypic/allele* frequency of the main class II HLA molecules

| Alleles | Frequency of individuals (%) | | | | | | |
|---|---|---|---|---|---|---|---|
| | France | Germany | USA Caucasian | USA black | Senegal | The Indies | Japan |
| DRB1*0101 | 17.7/9.3 | 13.0/6.7 | 14.1/7.3 | 3.8/1.9 | 1.2/0.6 | 7.5/3.8 | 9.6/4.9 |
| DRB1*0401 | 10.9/5.6 | 15.5/8.1 | 13.0/6.7 | 3.0/1.5 | 0.0/0.0 | 1.8/0.9 | 0.0/0.0 |
| DRB1*1101 | 17.6/9.2 | 17.6/9.2 | 8.6/4.4 | 15.7/8.2 | 17.7/9.3 | 1.8/0.9 | 4.0/2 |
| DRB1*0701 | 26.0/14.0 | 23.1/12.3 | 26.7/14.4 | 18.6/9.8 | 15.0/7.8 | 24.3/13 | 1.2/0.6 |
| DRB1*0301 | 20.6/10.9 | 17.9/9.4 | 18.1/9.5 | 13.5/7 | 19.4/10.2 | 10.3/5.3 | 0.8/0.4 |
| DRB1*1301 | 11.6/6.0 | 8.8/4.5 | 9.9/5.1 | 8.2/4.2 | 9.2/4.7 | 12.2/6.3 | 1.4/0.7 |
| DRB1*1501 | 15.4/8.0 | 15.0/7.8 | 19.5/10.3 | 16.5/8.6 | 0.0/0.0 | 22.7/12.1 | 17.4/9.1 |
| TOTAL | 86.3/63.0 | 82.4/58.0 | 82.1/57.7 | 65.4/41.2 | 54.6/32.6 | 66.7/42.3 | 32.3/17.7 |
| DRB5*0101 | 15.2/7.9 | 9.0/4.6 | 4.7/2.4 | 19.7/10.4 | 0.0/0.0 | 0.0/0.0 | 10.9/5.6 |
| DRB3*0101 | 17.6/9.2 | 18.6/9.8 | 19.7/10.4 | 27.9/15.1 | 13.3/6.9 | 9.6/4.9 | 12.6/6.5 |
| DRB4*0101 | 48.2/28.0 | 37.7/21.1 | 35.7/19.8 | 30.3/16.5 | 13.3/6.9 | 43.4/24.8 | 49.4/28.9 |
| TOTAL | 69.9/45.1 | 58.4/35.5 | 54.6/32.6 | 66.4/42.0 | 25.7/13.8 | 50.6/29.7 | 65.2/41.0 |
| DPB1*0401 | 64.0/40.0 | 61.7/38.1 | 43.9/25.1 | 20.8/11 | 9.4/4.8 | nd | 9.2/4.7 |
| DPB1*0402 | 20.8/11.0 | 28.4/15.4 | 23.6/12.6 | 17.2/9 | 44.5/25.5 | nd | 60.1/36.8 |
| TOTAL | 76.0/51.0 | 78.4/53.5 | 61.2/37.7 | 36.0/20 | 51.4/30.3 | nd | 65.8/41.5 |

*The predominant HLA II molecules (allele frequency > 5%) are indicated in bold

All the class II HLA molecules adopt a very similar three-dimensional structure. Their peptide-binding site is made up of a beta-sheet floor on which lie two alpha-helices. The site is open at the two ends and has five specificity pockets (P1, P4, P6, P7 and P9) corresponding to the positions of the peptide residues that they accommodate (Stern et al., Nature, 1994, 368, 215-221). The peptides which bind to class II HLA molecules generally have a size between 11 and 25 amino acids. Since the differences in sequences between class II HLA molecules are essentially located in the pockets of the peptide-binding site, the $CD4^+$ T epitopes vary from one individual to the other according to their class II HLA molecules.

In order to be efficient, the tumor-antigen-specific CD4+ T lymphocyte response must be of sufficient magnitude (or strength) while mobilizing a large number of lymphocytes and must take place in a majority of individuals.

Recent studies show that the magnitude of the CD4+ T lymphocyte response against an antigen (or specific CD4+ T response) is dependent on the size of the repertoire of CD4+ T lymphocytes specific for this antigen which circulate in the organism (Moon et al., Immunity, 2007, 27, 203-213). This repertoire size is very variable from one antigen to another. It results, on the one hand, from all the TCR rearrangements that can recognize the antigen and from thymic selection. It is possible to quantify the repertoire specific for an antigen by various methods which are based either on the use of class II HLA tetramers (Jenkins et al., J. Immunol., 2012, 188, 4135-4140), or on the amplification of CD4+ T lymphocytes by nonspecific stimulations (Geiger, et al., J. Exp. Med., 2009, 206, 1525-1534) or specific stimulations (Delluc et al., Blood, 2010, 116, 4542-4545; Delluc et al., Faseb J., 2011, 25, 2040-2048; international application WO 2010/076413). Since specific CD4+ T cells are present at a very low frequency in donor blood, the specific CD4+ T lymphocytes are amplified by cycles of antigenic stimulation; the peptide-specificity of the CD4+ T cells is evaluated after amplification. These tests have a predictive value for the strength of the specific CD4+ T lymphocyte response in humans and make it possible to identify the proteins or the peptides which have the largest repertoire of specific CD4+ T lymphocytes and which are therefore capable of stimulating the strongest specific CD4+ T lymphocyte responses. In addition, when carried out on a set of donors having varied class II HLA molecules, these tests make it possible to demonstrate the proteins, the peptides or the combinations of peptides which have a high responder frequency. Thus, the test for CD4+ T lymphocyte amplification via specific stimulations has made it possible to distinguish therapeutic antibodies that are immunogenic from those which are not (Delluc et al., Faseb J., 2011, 25, 2040-2048) and to reveal the immunogenicity of recombinant erythropoietin (Delluc et al., Blood, 2010, 116, 4542-4545).

Given the polymorphism of class II HLA molecules, the capacity of an antigen to stimulate specific CD4+ T lymphocytes in a majority of individuals depends on its capacity to be presented by numerous class II HLA molecules. This presentation capacity depends on the affinity of the peptide sequences present in the antigen for the class II HLA molecules, the CD4+ T epitopes being in fact mainly found in peptides of strong affinity. Since the binding specificity of class II HLA molecules is very variable from one class II HLA molecule to another, these peptides vary from one individual to another. However, certain peptides can bind to several molecules via a common zone of interaction with the class II HLA molecules. They can also house several zones of interaction with class II HLA molecules. The evaluation of the frequency of responders to an antigen or peptides derived from this antigen requires the polymorphism of class II HLA molecules to be taken into account. A first evaluation can be carried out by measuring the affinity of peptides derived from the antigen for the most frequent class II HLA molecules. This affinity can in particular be measured by means of binding tests specific for HLA-DR molecules (U.S. Pat. No. 6,649,166) and HLA-DP4 molecules (international application WO 03/040299). A more accurate evaluation is performed by means of a test for amplification of T lymphocytes by specific stimulations, carried out using a sufficient number of individuals having varied HLA II molecules to cover all the most frequent class II HLA molecules (international application WO 2010/076413).

Cyclin B1 (CCNB1) is a protein of 433 amino acids and of 48 kDa, involved in cell cycle regulation and more particularly in the transition from the G2 phase to the M phase. Human cyclin B1 corresponds to the UniProt sequence P14635 or SEQ ID No. 1. In a healthy cell, it associates during the G2 phase of the cell cycle with cyclin dependent kinase 1 (cdk1, also called cdc2) to form M-phase promoting factor (MPF). The activation of this complex during G2/M transition brings about its translocation into the nucleus, where it contributes to nuclear envelope fragmentation, to mitotic spindle assembly, to chromosome condensation and to chromatid segregation. CCNB1 is then rapidly degraded by ubiquitination and destruction by the proteasome, thereby enabling cdc2 inactivation and exit from mitosis. CCNB1 expression in healthy cells is therefore transient. CCNB1 synthesis is initiated at the end of the S phase, then gradually increases during the G2 phase and reaches a peak at the level of G2/M transition, before being stopped. CCNB1 is kept in the cytoplasm throughout the G2 phase, before becoming nuclear at the beginning of mitosis (G2/M transition).

CCNB1 is overexpressed in numerous cancers, including breast cancer (Ohta et al., Breast Cancer, 1997, 4, 17-24), colon cancer (Wang et al., J. Cancer Res. Clin. Oncol., 1997, 123, 124-127), prostate cancer (Mashal et al., Cancer Res., 1996, 56, 4159-4163), esophageal cancer (Murakami et al., Virchows Archiv: An International Journal of Pathology, 1999, 434, 153-158), stomach cancer (Yasuda et al., J. Cancer Res. Clin. Oncol., 2002, 128, 412-416), lung cancer (Soria et al., Cancer Res., 2000, 60, 4000-4004) and ENT cancers (Hoffmann et al., Anticancer research, 2011, 31, 3151-3157). In tumor cells, cyclin B1 is found both in the nucleus and in the cytoplasm. This abnormal expression contributes to tumor growth (Keyomarsi et al., Proc. Natl. Acad. Sci. USA, 1993, 90, 1112-1116), as shown by experiments in which its expression is inhibited (Yuan et al., Oncogene, 2004, 23, 5843-5852). This overexpression appears to be due to the loss of function of the p53 protein (Yu et al., Mol. Immunol., 2002, 38, 981-987). Cyclin B1 represents a target of choice for the development of a cancer vaccine given that it is frequently expressed in varied cancers and essential for tumor growth, but transiently expressed in healthy cells, which is favorable to a low induction of tolerance.

Several studies have shown that cyclin B1 (CCNB1) can be the target of an immune response. Peptides derived from cyclin B1, eluted from class I HLA molecules extracted from tumor cells of various origins (Kao et al., J. Exp. Med., 2001, 194, 1313-1323), are capable of inducing a specific-CTL response (Table II; Kao et al., J. Exp. Med., 2001, 194, 1313-1323; Sorensen et al., Clin. Cancer Res., 2009, 15, 1543-1549; Andersen et al., Cancer Immunol. Immunother., 2001, 60, 227-234; international application WO 03/033520).

TABLE II

Published CCNB1 T epitopes (SEQ ID NOs: 96 to 109)

| Peptides | Sequences | Restriction | References |
|---|---|---|---|
| CD8+ T epitopes | | | |
| P1 | AGYLMELCV | HLA-A2 | Kao et al., mentioned |
| P2 | AGYLMELCM | HLA-A2 | above |
| P3 | AGYLMELCF | HLA-A2 | |
| P4 | AGYLMELCC | HLA-A2 | WO 03/033520 |
| P5 | AGYLMELCMA | HLA-A2 | |
| P6 | AGYLMELCFA | HLA-A2 | |
| CB9 (323-331) | AKYLMELTM | HLA-A2 | |
| CB10 (323-332) | AKYLMELTML | HLA-A2 | |
| CB9L2 | ALYLMELTM | HLA-A2 | Sorensen et al., |
| CB9M2 | AMYLMELTM | HLA-A2 | mentioned above |
| CB204 (204-212) | ILIDWLVQV | HLA-A2 | Andersen et al., mentioned above |
| CD4+ T epitopes | | | |
| 215-229 | KFRLLQETMYMTVSI | Unknown | |
| 219-233 | LQETMYMTVSIIDRF | Unknown | (Vella et al., Proc. Natl. Acad. Sci. USA, 2009, 106, 14010-14015). |
| 223-234 | MYMTVSIIDRFM | Unknown | Application US 2011/0280897 |

A spontaneous humoral response directed against CCNB1 and, a priori, CD4+-lymphocyte-dependent has been observed in patients suffering from cancer (Suzuki et al., Clin. Cancer. Res., 2005, 11, 1521-1526). Tests for stimulation of CD4+ T lymphocytes with overlapping peptides of CCNB1 (12-15 amino acids) have shown that only three peptides (CCNB1 215-229, 219-233 and 223-234) covering region 215 to 233 of the protein were capable of activating CD4+ T and CD8+ T lymphocytes in several healthy individuals (Vella et al., Proc. Natl. Acad. Sci. USA, 2009, 106, 14010-14015).

However, the actual efficacy of this peptide has not been demonstrated given that the frequency of responders was determined on individuals of unknown HLA haplotype, i.e. without taking into account the HLA II molecule polymorphism. In addition, the strength of the CD4+ T response to these peptides is not known given that only a qualitative analysis of the CD4+ T response to these peptides is carried out.

In order to develop vaccines which are effective against cancer, there is therefore a real need to have new CD4+ T epitopes of cyclin B1 that are capable of inducing an effective CD4+ T response, i.e. a response of high strength and in numerous individuals.

The inventors have identified a set of CD4+ T epitopes of human cyclin B1 which are immunodominant in vitro and which are different from the three CD4+ T epitopes of region 215-233 that have previously been described (Table IV). These CD4+ T epitopes of cylin B1 which are immunodominant in vitro contribute to the CD4+ T response directed against cyclin B1, insofar as they are specifically recognized by CD4+ T lymphocytes generated by stimulation with the cyclin B1 protein. Contrary to the prior art CD4+ T epitopes, the restriction of which with respect to HLA II molecules is unknown, these CD4+ T epitopes which are immunodominant in vitro are recognized in individuals carrying varied HLA II molecules comprising all the HLA-DRB1 molecules that are the most frequent in the Caucasian population (HLA-DR1, -DR3, -DR4, -DR7, -DR11, -DR13 and -DR15; Tables I and IV). The inventors have also identified peptides which have a broad specificity for binding to the HLA II molecules which are the most frequent in the Caucasian population (Table VI).

Notably, the peptides which are immunodominant in vitro include the peptides which are the most effective, i.e. capable of inducing the most effective specific CD4+ T response (average strength of the response in vitro greater than 2.8% and which can reach 6.1% and frequency of responder in vitro greater than 65% and which can reach 85%; Table IX), in a population of individuals carrying varied HLA II molecules, comprising all the HLA-DRB1 molecules that are the most frequent in the Caucasian population, covering by themselves 80% of the individuals of the Caucasian population.

Such peptides represent particularly promising candidates for the development of a cancer vaccine, owing to the fact that they are derived from cyclin B1 and that they are capable of inducing a specific CD4+ T response of strong magnitude in vitro in numerous individuals.

Consequently, a subject of the present invention is an isolated peptide, consisting essentially of a sequence of from 11 to 30 amino acids, preferably from 15 to 25 amino acids, which is derived from the human cyclin B1 sequence of SEQ ID No. 1 and which comprises at least one human cyclin B1 CD4+ T epitope which is immunodominant in vitro, said peptide being capable of stimulating a specific human CD4+ T lymphocyte response.

Definitions

The term "cyclin B1" or "CCNB1" is intended to mean a cyclin B1 protein derived from any mammal; preferably, it is the human cyclin B1 protein. Human cyclin B1 corresponds to the UniProt amino acid sequence P14635 or SEQ ID No. 1.

The term "CD4+ T epitope" is intended to mean a peptide of from 11 to 25 amino acids which binds at least one HLA II molecule, preferably one predominant HLA II molecule as presented in Table I, and is recognized by specific CD4+ T lymphocytes in individuals carrying this HLA II molecule; the peptide comprises a sequence of 9 amino acids including the residues for anchoring to the HLA II molecules, flanked by at least 1 amino acid, preferably at least 2 or 3 amino acids at each of its ends.

The term "cyclin B1 CD4+ T epitope which is immunodominant in vitro" is intended to mean a cyclin B1 CD4+ T epitope which is recognized by human CD4+ T lymphocytes previously stimulated in vitro by means of at least two successive cycles, preferably 3 or 4 successive cycles, of stimulation by autologous antigen-presenting cells exhibiting the cyclin B1 protein, in particular autologous dendritic cells loaded with the cyclin B1 protein.

The term "predominant HLA II molecule" is intended to mean an HLA II molecule of which the allele frequency is greater than 5% in the reference population.

The term "cancer" is intended to mean a cancer associated with the overexpression of the cyclin B1 protein by tumor cells, such as, in a nonlimiting manner: breast cancer, colon cancer, prostate cancer, esophageal cancer, stomach cancer, lung cancer and ENT cancers.

The term "frequency of responders in vitro to a peptide according to the present invention" is intended to mean the percentage of individuals for whom CD4+ T lymphocyte lines specific for said peptide have been obtained relative to all the individuals tested.

The frequency of responders can be determined according to the method described in Application WO 2010/076413.

The term "strength of the in vitro response to a peptide according to the present invention" is intended to mean the strength of the in vitro response of human CD4+ T lymphocytes specific to said peptide, i.e. the percentage of culture wells containing CD4+ T lymphocytes specific for said peptide relative to all the wells placed in culture. The average strength of the response to a peptide according to the invention corresponds to the average, over all of the donors, of the strengths calculated for each donor.

The strength of the response can be determined according to the method described in Application WO 2010/076413.

The percentage identity of an amino acid sequence is defined by the percentage of amino acid residues in a sequence to be compared which are identical to a reference sequence after alignment of the sequences, with spaces being introduced if necessary, in order to obtain a maximum sequence identity. The percentage identity is then determined according to the following formula: percentage identity=100×[1−(C/R)], such that C is the number of differences between the reference sequence and the sequence to be compared over the entire length of the reference sequence, (i) each amino acid in the reference sequence which does not have a corresponding amino acid aligned in the sequence to be compared, (ii) each space in the reference sequence and (iii) each amino acid aligned in the reference sequence which is different than an amino acid in the sequence to be compared constitutes a difference, and R is the number of amino acids in the reference sequence over the entire length of the alignment with the sequence to be compared (i.e. the entire length of the reference sequence), each space generated in the reference sequence being counted as an amino acid. The sequence alignment for the purpose of determining the percentage identity of a sequence can be carried out in various ways known to those skilled in the art, for example using available public software such as BLAST (Altschul et al., J. Mol. Biol., 1990, 215, 403-). This software is preferably used with default parameters.

The invention encompasses recombinant or synthetic peptides as defined above. The binding activity of the peptides of the invention with respect to HLA II molecules is measured by means of a conventional test for specific binding of HLA II molecules, such as a competition test with immunoenzymatic visualization, as described in American patent U.S. Pat. No. 6,649,166 and PCT international application WO 03/040299, respectively for the HLA-DR and HLA-DP4 molecules. The capacity of the peptides of the invention to induce a specific CD4+ T lymphocyte response from precursors present in naive individuals, and to stimulate such specific cells in individuals suffering from a cancer associated with the overexpression of cyclin B1, the specificity of the induced CD4+ T lymphocytes, with respect to the cyclin B1 peptides or protein, and also the capacity of the peptides of the invention to be recognized by specific CD4+ T lymphocytes, are evaluated according to the standard techniques known to those skilled in the art, for instance: a cell proliferation test, an ELISPOT test (assaying of cytokine-producing cells) or an intracellular cytokine assay, specific for a cytokine such as IFN-γ, IL-2, IL-4 or IL-10.

The amino acids are denoted using the one-letter code. The positions of the peptides derived from cyclin B1 are indicated with reference to the human sequence (SEQ ID No. 1).

According to one advantageous embodiment of said peptide, it binds to at least three, preferably at least 4, different predominant HLA II molecules, preferably chosen from HLA-DR1, HLA-DR3, HLA-DR4, HLA-DR7, HLA-DR11, HLA-DR13, HLA-DR15, HLA-DRB3, HLA-DRB4, HLA-DRB5, HLA-DP401 and HLA-DP402 molecules. Preferably, said HLA II molecules are encoded respectively by the HLA DRB1*0101, DRB1*0301, DRB1*0401, DRB1*0701, DRB1*1101, DRB1*1301, DRB1*1501, DRB3*0101, DRB4*0104, DRB5*0101, DP*0401 and DP*0402 alleles.

According to another advantageous embodiment of said peptide, the frequency of responders in vitro to said peptide is at least 55%, preferably at least 65%, preferably at least 75%, in a group of human individuals expressing varied HLA II molecules including the HLA II molecules predominant in the population from which said individuals are derived, preferably at least the HLA-DR1, HLA-DR3, HLA-DR4, HLA-DR7, HLA-DR11, HLA-DR13 and HLA-DR15 molecules.

According to another advantageous embodiment of said peptide, the average strength of the in vitro response of human CD4+ T lymphocytes specific for said peptide is at least 2.5%, preferably at least 2.8%, in a group of human individuals expressing varied HLA II molecules including the HLA II molecules predominant in the population from which said individuals are derived, preferably at least the HLA-DR1, HLA-DR3, HLA-DR4, HLA-DR7, HLA-DR11, HLA-DR13 and HLA-DR15 molecules.

According to one advantageous arrangement of the above embodiments, the frequency of responders in vitro to said peptide is at least 55%, preferably at least 65%, preferably at least 75%, in a group of human individuals expressing varied HLA II molecules including the HLA II molecules predominant in the population from which said individuals are derived, preferably at least the HLA-DR1, HLA-DR3, HLA-DR4, HLA-DR7, HLA-DR11, HLA-DR13 and HLA- DR15 molecules, and the average strength of the in vitro response of human CD4+ T lymphocytes specific for said peptide is at least 2.5%, preferably at least 2.8%, in said group of human individuals.

According to another advantageous embodiment of said peptide, it is selected from the group made up of:
a) the sequences of 11 to 30 (11, 12, 13, 14, 15, 16, 17, 18, 19, 20, 21, 22, 23, 24, 25, 26, 27, 28, 29 or 30) consecutive amino acids of the human cyclin B1 sequence of SEQ ID No. 1, preferably of 15 to 25 (15, 16, 17, 18, 19, 20, 21, 22, 23, 24, 25) consecutive amino acids of said sequence, comprising at least residues 3 to 11, 19 to 27, 27 to 35, 120 to 128, 282 to 290, 287 to 295, 305 to 313, 317 to 325, 322 to 330, 325 to 333, 376 to 384, 379 to 387, 412 to 420, 418 to 426 or 422 to 430 of said sequence SEQ ID No. 1, and
b) the sequences of 11 to 30 (11, 12, 13, 14, 15, 16, 17, 18, 19, 20, 21, 22, 23, 24, 25, 26, 27, 28, 29 or 30) amino acids, preferably of 15 to 25 (15, 16, 17, 18, 19, 20, 21, 22, 23, 24, 25) amino acids, having at least 70% identity, preferably at least 75%, 80%, 85% or 90%, preferably at least 95% identity, with a sequence in a), with the exclusion of the sequence of 15 amino acids made up of residues 279 to 293 of said sequence SEQ ID No. 1.

The invention encompasses the natural or synthetic variant peptides obtained by mutation (insertion, deletion, substitution) of one or more amino acids in the cyclin B1 sequence, provided that said peptide derived from the human cyclin B1 sequence of SEQ ID No. 1 retains its properties of cyclin B1 CD4+ T epitope which is immunodominant in vitro and is capable of binding HLA II molecules, in particular predominant HLA II molecules, and of stimulating a cyclin-B1-specific human CD4+ T lymphocyte response, i.e. they are recognized by CD4+ T lymphocytes specific for the wild-type sequence or for a natural variant of cyclin B1. The natural variants result in particular from the polymorphism of cyclin B1. In addition, other variants can be easily constructed, given that the amino acid residues involved in binding to HLA-DR and HLA-DP4 molecules (anchoring residues) and the effect of modifications of these residues on the binding to HLA-DR and HLA-DP4 molecules are known to those skilled in the art; PCT international application WO 03/040299 teaches in particular that, for HLA-DP4 binding, the residue in P6 must be aromatic or hydrophobic or consist of a cysteine residue (C), and at least one of the residues P1 and P9 is such that P1 is aromatic or hydrophobic and/or P9 is aromatic or hydrophobic or consists of a C, D, Q, S, T or E residue, while the residue in P4 may be any amino acid residue. American patent U.S. Pat. No. 6,649,166 describes a general method for determining the residues for anchoring to HLA DR molecules (P1, P4, P6, P7 and P9) and the nature of the mutations of these residues which make it possible to modify the affinity for HLA DR molecules. HLA-DR-molecule-binding motifs are described in particular in Sturnolio et al., Nat. Biotech, 1999, 17, 533-534 and Rammensee et al., Immunogenetics, 1995, 41, 178-228. The variant may also comprise the substitution of one or more cysteine residues of cyclin B1 with another amino acid, for example a serine.

According to one advantageous arrangement of this embodiment, said peptide is selected from the group made up of:
the sequences of 11 to 30 (11, 12, 13, 14, 15, 16, 17, 18, 19, 20, 21, 22, 23, 24, 25, 26, 27, 28, 29 or 30) consecutive amino acids of the human cyclin sequence of SEQ ID No. 1, preferably of 15 to 25 (15, 16, 17, 18, 19, 20, 21, 22, 23, 24, 25) consecutive amino acids of said sequence, comprising at least residues 3 to 11, 282 to 290, 287 to 295, 305 to 313, 376 to 384, 418 to 426 or 422 to 430 of said sequence SEQ ID No. 1,
the sequences of 15 to 30 (15, 16, 17, 18, 19, 20, 21, 22, 23, 24, 25, 26, 27, 28, 29 or 30) consecutive amino acids of the human cyclin sequence of SEQ ID No. 1, preferably of 15 to 25 (15, 16, 17, 18, 19, 20, 21, 22, 23, 24, 25) consecutive amino acids of said sequence, comprising at least residues 301 to 313 or 418 to 430 of said sequence SEQ ID No. 1, and
the sequences of 16 to 30 (16, 17, 18, 19, 20, 21, 22, 23, 24, 25, 26, 27, 28, 29 or 30) consecutive amino acids of the human cyclin sequence SEQ ID No. 1, preferably of 16 to 25 (16, 17, 18, 19, 20, 21, 22, 23, 24, 25) consecutive amino acids of said sequence, comprising at least residues 282 to 295 of said sequence SEQ ID No. 1.

According to another advantageous arrangement of this embodiment, said peptide comprises or consists of a sequence selected from the group made up of the sequences SEQ ID Nos.: 10, 12, 13, 26, 57, 58, 61, 63, 64, 65, 76, 77, 82, 83, 84, 87, 88, 89 and 91. Preferably, said peptide comprises or consists of a sequence selected from the group made up of the sequences SEQ ID Nos.: 10, 57, 58, 61, 76, 83, 84, 87, 88 and 91.

Said peptide advantageously comprises several CD4+ T epitopes of the cyclin B1 protein.

A subject of the invention is also a mixture of peptides, isolated or combined with one another, in particular in the form of a multi-epitope polypeptide, said mixture comprising: (i) at least one first peptide comprising at least one cyclin B1 CD4+ T epitope which is immunodominant in vitro, as defined above, and (ii) at least one second peptide comprising at least one CD4+ T epitope other than said immunodominant epitope, and/or one CD8+ T epitope, and/or one B epitope, in particular CD4+ T and/or CD8+ T epitopes of cyclin B1 and/or of other tumor antigens, such as, in particular, MAGE, NY-ESO-1, survivin and midkine.

The CD4+ T or CD8+ T epitopes derived from tumor antigens are in particular described on the website www.cancerimmunity.org/peptidedatabase/tumor-specific.htm and in PCT international applications WO 2007/036638 and WO 2009/153463.

Among the epitopes which can be incorporated into the mixture of the invention, mention may in particular be made of:
cyclin B1 CD8+ T epitopes as defined above (Table II),
the MAGE CD8+ T epitopes as described in U.S. Pat. No. 6,063,900 and PCT application WO 2004/052917,
the MAGE CD4+ T epitopes such as DR1-restricted MAGE-A3 267-282 (PCT international application WO 02/095051); DR4- and DR7-restricted MAGE-A3 149-160 (Kobayashi et al., Cancer Research, 2001, 61, 4773-4778); DR11-restricted MAGE-A3 191-205 and 281-295 (Consogno et al., Blood, 2003, 101, 1038-1044; Manici et al., J. Exp. Med., 1999, 189, 871-876) and DR13-restricted MAGE-A3 121-134 (U.S. Pat. No. 6,716,809); DR15-restricted MAGE-A1 281-292 (PCT international application WO 00/78806); DR4-restricted MAGE-A6 102-116, 121-144, 140-170, 145-160, 150-165 and 246-263 (Tatsumi et al., Clinical Cancer Research, 2003, 9, 947-954); DR15-restricted MAGE-A1 281-292 (PCT international application WO 00/78806); DR4-restricted MAGE-A6 102-116, 121-144, 140-170, 145-160, 150-165 and 246-263 (Tatsumi et al., Clinical Cancer Research, 2003, 9, 947-954) and the HLA-DP4-restricted MAGE epitopes as described in PCT international application WO 2007/026078, a survivin CD8+ T epitope chosen from: survivin 96-104 (LTLGEFLKL, SEQ ID No. 92) or 95-104 (ELTLGEFLKL, SEQ ID No. 93), survivin-2B 80-88 (AYACNTSTL, SEQ ID No. 94) and the peptides as described in Table I of Bachinsky et al., Cancer Immun., 2005, 5, 6-, a survivin CD4+ T epitope as described in PCT international application WO 2007/036638 and in particular peptide 19-33, 90-104 or 93-107, a midkine CD4+ T and/or CD8+ T epitope as described in PCT international application WO 2009/153463, a natural or synthetic universal CD4+ T epitope such as the tetanus toxin peptide TT 830-846 (O'Sullivan et al., J. Immunol., 1991, 147, 2663-2669), the influenza virus hemagglutinin peptide HA 307-319 (O'Sullivan et al., mentioned above), the PADRE peptide (KXVAAWTLKAA, SEQ ID No. 95; Alexander et al., Immunity, 1994, 1, 751-761) and peptides derived from the *Plasmodium falciparum* antigens, such as the peptide CS.T3 (Sinigaglia et al., Nature, 1988, 336, 778-780) and the peptides CSP, SSP2, LSA-1 and EXP-1 (Doolan et al., J. Immunol., 2000, 165, 1123-1137), a B epitope made up of a sugar (Alexander et al., mentioned above), said B epitope preferably being in the form of a glycopeptide, and a B epitope of cyclin B1, specifically recognized by antibodies directed against said tumor antigen.

According to one embodiment of said mixture, the second peptide is a peptide comprising a cyclin B1 CD4+ T epitope capable of binding to at least 3, preferably at least 6, different predominant HLA II molecules as defined above.

Advantageously, said second peptide is a peptide capable of binding to at least 6 different predominant HLA II molecules as defined above, selected from the group made up of:

a) the sequences of 11 to 30 (11, 12, 13, 14, 15, 16, 17, 18, 19, 20, 21, 22, 23, 24, 25, 26, 27, 28, 29 or 30) consecutive amino acids of the human cyclin B1 sequence of SEQ ID No. 1, preferably of 15 to 25 (15, 16, 17, 18, 19, 20, 21, 22, 23, 24, 25) consecutive amino acids of said sequence, comprising at least residues 170-178, 201-209, 204-212, 209-217, 214-222, 218-226, 223-231, 227-235, 243-251, 246-254, 252-260, 269-277, 301-309, 344-352, 365-373, 368-376 or 371-379 of said sequence SEQ ID No. 1, and b) the sequences of 11 to 30 (11, 12, 13, 14, 15, 16, 17, 18, 19, 20, 21, 22, 23, 24, 25, 26, 27, 28, 29 or 30) amino acids, preferably of 15 to 25 (15, 16, 17, 18, 19, 20, 21, 22, 23, 24, 25) amino acids, having at least 70% identity, preferably at least 75%, 80%, 85% or 90%, preferably at least 95% identity with a sequence in a).

Preferably, said peptide capable of binding to at least 6 different predominant HLA II molecules comprises or consists of a sequence selected from the group made up of: SEQ ID NOs: 33, 39, 40, 41, 42, 43, 44, 45, 48, 49, 50, 54, 60, 69, 73, 74, 75, 85, 86 and 90.

Alternatively, said second peptide is a peptide capable of binding to 3 to 5 different predominant HLA II molecules, which is selected from the group made up of:

a) the sequences of 11 to 30 (11, 12, 13, 14, 15, 16, 17, 18, 19, 20, 21, 22, 23, 24, 25, 26, 27, 28, 29 or 30) consecutive amino acids of the human cyclin B1 sequence of SEQ ID No. 1, preferably of 15 to 25 (15, 16, 17, 18, 19, 20, 21, 22, 23, 24, 25) consecutive amino acids of said sequence, comprising at least residues 115-123, 146-154, 166-174, 172-180, 187-195, 191-199, 197-205, 239-247, 266-274, 271-279, 277-285, 293-301, 329-337, 361-369 or 387-395 of said sequence SEQ ID No. 1, and b) the sequences of 11 to 30 (11, 12, 13, 14, 15, 16, 17, 18, 19, 20, 21, 22, 23, 24, 25, 26, 27, 28, 29 or 30) amino acids, preferably of 15 to 25 (15, 16, 17, 18, 19, 20, 21, 22, 23, 24, 25) amino acids, having at least 70% identity, preferably at least 75%, 80%, 85% or 90%, preferably at least 95% identity with a sequence in a).

Preferably, said peptide capable of binding to 3 to 5 different predominant HLA II molecules comprises or consists of a sequence selected from the group made up of: SEQ ID NOs: 25, 29, 32, 34, 36, 37, 38, 47, 53, 55, 56, 59, 66, 72 and 78.

The combination of cyclin B1 CD4+ T epitope(s) as defined above advantageously makes it possible to improve the antitumor immune response by broadening the coverage of responder individuals and by strengthening the magnitude of the immune response.

According to another advantageous embodiment of said mixture, it involves a multi-epitope polypeptide comprising the concatenation of the peptides comprising the various epitopes. In accordance with the invention, the sequences of the various peptides are linked to one another by a peptide bond or separated by exogenous sequences. The multi-epitope derivative comprises fewer than 100 consecutive amino acids of cyclin B1, preferably fewer than 50, preferably fewer than 30. The multi-epitope peptide derivative has a length of from 20 to 200 amino acids, preferably from 30 to 100 amino acids, preferably of approximately 50 amino acids.

A subject of the present invention is also a modified peptide or polypeptide derived from the above peptide or polypeptide through the introduction of any modification at the level of the amino acid residue(s), of the peptide bond or of the ends of the peptides, provided that said modified peptide or polypeptide is capable of binding to HLA II molecules and of activating specific human CD4+ T lymphocytes. This or these modification(s), preferably one or more chemical modification(s), which are introduced into the peptides by conventional methods known to those skilled in the art, include, in a nonlimiting manner, at least one of the following chemical modifications: acetylation of the N-terminal amino acid residue and/or amidation of the C-terminal amino acid residue (Maillére et al., Molecular Immunology, 1195, 32, 1377-1385), substitution of an amino acid with a non-proteinogenic amino acid (D amino acid or amino acid analog); addition of a chemical group (lipid, oligosaccharide or polysaccharide) at the level of a reactive function, in particular of the side chain R; modification of the peptide bond (—CO—NH—), in particular with a bond of the retro or retro-inverso type (—NH—CO—) or a bond other than the peptide bond; cyclization; fusion of the sequence of said peptide with that of a peptide (epitope of interest for vaccination; tag of use for purifying the peptide, in particular in a form cleavable by a protease); fusion of the sequence of said peptide with that of a protein, in particular an α-chain of an HLA I or HLA II molecule, a β-chain of an HLA II molecule or the extracellular domain of said chain or else a sequence for targeting to the endosome derived in particular from the invariable chain Ii or from the LAMP-1 protein; coupling to an appropriate molecule, in particular a label, for example a fluorochrome or biotin. These modifications are intended in particular to increase the stability and more particularly the resistance to proteolysis, and also the solubility, or the immunogenicity, or to facilitate the purification or the detection either of the peptide according to the invention, or of CD4+ and/or CD8+ cells specific for said peptide.

For the purposes of the present invention, the term "peptide derivative" is intended to mean a peptide according to the invention, a modified peptide or a modified or unmodified multi-epitope polypeptide.

According to one advantageous embodiment of said modified peptide or polypeptide, it comprises one or more N6-acetyl-lysine(s), phosphoserine(s) and/or phosphothreonine(s). Preferably, the N-acetyl-lysine is in position 73, the phosphoserine(s) are in position 126, 128, 133 and/or 147 and the phosphothreonine is in position 321 of the sequence SEQ ID No. 1.

According to another advantageous embodiment of said modified peptide or polypeptide, it comprises the acetylation of its N-terminal amino acid residue and/or the amidation of its C-terminal amino acid residue.

According to another advantageous embodiment of said modified peptide or polypeptide, it advantageously comprises a tag fused to one of its ends, for the purification or detection of said peptide/polypeptide. The tag, in particular a polyhistidine sequence or a B epitope of an antigen, is preferably separated from the sequence of the peptide/polypeptide by a cleavage site for a protease so as to isolate the peptide/polypeptide sequence from the fusion.

According to another advantageous embodiment of said modified peptide or polypeptide, it is a lipopeptide or a lipopolypeptide comprising, respectively, a peptide and a polypeptide as defined above.

Said lipopeptide/polypeptide is in particular obtained by addition of a lipid to an α-amino function or to a reactive function of the side chain of an amino acid of said peptide or polypeptide; it may comprise one or more optionally branched or unsaturated chains derived from $C_4$-$C_{20}$ fatty acids (palmitic acid, oleic acid, linoleic acid, linolenic acid, 2-aminohexadecanoic acid, pimelautide, trimexautide) or a derivative of a steroid. The preferred lipid portion is in particular represented by an $N^\alpha$-acetyl-lysine $N^\epsilon$(palmitoyl) group, also called Ac-K(Pam).

According to yet another advantageous embodiment of said modified peptide or polypeptide, it is a fusion protein comprising said peptide or polypeptide fused with a heterologous protein (other than cyclin B1) or a heterologous polypeptide fragment (fragment of a protein other than cyclin B1 or fragment of cyclin B1 of which the sequence is not directly adjacent to the sequence of said peptide or polypeptide in the sequence of said cyclin B1).

The peptide or the polypeptide fragment may be fused with the $NH_2$ or COOH end of said heterologous protein or of said heterologous polypeptide fragment or inserted into the sequence of said protein or of said fragment.

According to one advantageous disposition of said fusion protein, it is made up of a peptide or a polypeptide as defined above, fused with a sequence for targeting to the endosome, preferably derived from a human invariable chain Ii or from the LAMP-1 protein. The sequences for targeting to the endosome and the use thereof for targeting antigens to the endosome are in particular described in Sanderson et al. (Proc. Nat. Acad. Sci. USA, 1995, 92, 7217-7222), Wu et al. (Proc. Nat. Acad. Sci. USA, 1995, 92, 11671-11675) and Thompson et al. (J. Virol., 1998, 72, 2246-2252).

According to another advantageous arrangement of said fusion protein, it is made up of a peptide or a polypeptide as defined above, fused with one of the chains of an HLA molecule, preferably the beta-chain of an HLA II molecule or the alpha-chain of an HLA I molecule, or else with a fragment thereof corresponding to a soluble HLA molecule, in particular a fragment corresponding to the extracellular domain preceded by the homologous signal peptide or by a heterologous signal peptide. Said peptide is advantageously inserted between the signal peptide and the $NH_2$ end of the extracellular domain of the α- or β-chain, as described for the HLA-DR molecule (Kolzin et al., PNAS, 2000, 97, 291-296).

According to yet another advantageous arrangement of said fusion protein, it is made up of a peptide or a polypeptide as defined above, fused with a protein facilitating purification thereof or detection thereof, known to those skilled in the art, such as in particular glutathione-S-transferase (GST) and fluorescent proteins (GFPs and derivatives). In this case, the sequence of the peptide or of the polypeptide is preferably separated from the rest of the protein by a cleavage site for a protease, in order to facilitate the purification of said peptide or polypeptide of said polypeptide.

A subject of the present invention is also an isolated polynucleotide encoding a peptide, a polypeptide or a fusion protein as defined above.

In accordance with the invention, the sequence of said polynucleotide is that of the cDNA encoding said peptide or polypeptide or said fusion protein. Said sequence may advantageously be modified in such a way that the codon usage is optimum in the host in which it is expressed.

A subject of the present invention is also a recombinant vector comprising said polynucleotide.

For the purposes of the present invention, the term "vector" is intended to mean a nucleic acid molecule capable of transporting another nucleic acid to which it is linked. One type of vector which can be used in the present invention includes, in a nonlimiting manner, a linear or circular DNA or RNA molecule consisting of chromosomal, non-chromsomal, synthetic or semi-synthetic nucleic acids, such as in particular a viral vector, a plasmid or an RNA vector.

Numerous vectors into which a nucleic acid molecule of interest can be inserted in order to introduce it into and maintain it in a eukaryotic or prokaryotic host cell are known in themselves; the choice of an appropriate vector depends on the use envisioned for this vector (for example, replication of the sequence of interest, expression of this sequence, maintaining of this sequence in extrachromosomal form, or else integration into the chromosomal material of the host), and also on the nature of the host cell. For example, naked nucleic acids (DNA or RNA) or viral vectors such as adenoviruses, retroviruses, lentiviruses and AAVs, into which the sequence of interest has been previously inserted may be used; said sequence (isolated or inserted into a plasmid vector) can also be combined with a substance which allows it to cross the host cell membrane, such as a transporter, for instance a nanotransporter or a preparation of liposomes, or of cationic polymers, or else makes it possible to introduce it into said host cell using physical methods such as electroporation or microinjection. In addition, these methods can advantageously be combined, for example using electroporation combined with liposomes.

Preferably, said vector is an expression vector comprising all the elements required for the expression of the peptide, polypeptide or fusion protein as defined above. For example, said vector comprises an expression cassette including at least one polynucleotide as defined above, under the control of appropriate regulatory sequences for transcription and optionally for translation (promoter, enhancer, intron, start codon (ATG), stop codon, polyadenylation signal, splice site).

A subject of the present invention is also a modified prokaryotic or eukaryotic host cell comprising a peptide, a polypeptide, a fusion protein, a polynucleotide or a vector as defined above, it being possible for the cell to be stably or transiently modified. The cell is in particular an antigen-presenting cell such as a dendritic cell.

A subject of the present invention is also an immunogenic or vaccine composition, characterized in that it comprises at least one peptide or one mixture of peptides (isolated peptides or multi-epitope polypeptide), which has optionally been modified (lipopeptide, fusion protein), or a vector, as defined above, and a pharmaceutically acceptable vehicle, a carrier substance or an adjuvant.

The vaccine composition according to the invention advantageously comprises a pharmaceutically acceptable vehicle, a carrier substance and/or an adjuvant.

The pharmaceutically acceptable vehicles, the carrier substances and the adjuvants are those conventionally used.

The adjuvants are advantageously chosen from the group made up of: oily emulsions, mineral substances, bacterial extracts, oligonucleotides containing CpGs, saponin, alumina hydroxide, monophosphoryl-lipid A and squalene.

The carrier substances are advantageously selected from the group made up of: unilamellar or multilamellar liposomes, ISCOMs, virosomes, virus-like particles, saponin micelles, solid microspheres which are saccharide (poly(lactide-co-glycolide)) or gold-bearing in nature, and nanoparticles.

The vaccine composition comprises an effective dose of peptide, mixture of peptides or vector which makes it possible to obtain a prophylactic/therapeutic effect on the cancer associated with tumor overexpression of cyclin B1 as defined above. This dose is determined and adjusted to factors such as age, sex and weight of the subject. The vaccine composition is generally administered according to the usual vaccination protocols, at doses and for a period sufficient to induce a cellular response directed against the cyclin B1 protein. The administration may be subcutaneous, intramuscular, intravenous, intradermal, intraperitoneal, oral, sublingual, rectal, vaginal, intranasal, by inhalation or by transdermal application.

The composition is in a galenical form suitable for a chosen administration: injectable sterile solution, powder, tablets, gel capsules, suspension, syrup, suppositories, which are prepared according to standard protocols.

According to one advantageous embodiment of said composition, it comprises at least one cyclin B1 CD4$^+$ T epitope and one cyclin B1 CD8$^+$ T epitope, in the form of a mixture of peptides, preferably a multi-epitope polypeptide, or of an expression vector encoding said peptides or said polypeptide, as defined above.

The peptides according to the present invention and the derived products (mixture of peptides, in particular multi-epitope polypeptide; fusion protein, lipopeptide, recombinant vector) can be used in immunotherapy in the treatment of tumors overexpressing cyclin B1. Said peptides or derived products are used either as a vaccine, or in cell therapy, or else through a combination of the two approaches.

Cell therapy comprises the preparation of antigen-presenting cells (dendritic cells) by a conventional protocol comprising the isolation of peripheral blood mononuclear cells (PBMCs) from a patient to be treated and the culturing of the dendritic cells in the presence of peptide(s) or of peptide derivative(s) as defined above. In a second step, the antigen-presenting cells loaded with the peptide or derivative thereof are reinjected into the patient.

A subject of the present invention is also a prophylactic or therapeutic antitumor vaccination method, characterized in that it comprises the administration of a vaccine composition as defined above, to an individual, by any appropriate means as defined above.

A subject of the present invention is also the use of a peptide, of a mixture of peptides or of a vector, as defined above, for preparing a medicament (prophylactic or curative vaccine) intended for the prophylactic or curative immunotherapy of a cancer associated with overexpression of cyclin B1.

A subject of the present invention is also the use of at least one peptide as defined above, for preparing a reagent for immunomonitoring the cellular response against cyclin B1, intended for the evaluation of the prognosis or for the monitoring of the treatment of a cancer (surgery, radiotherapy, chemotherapy, immunotherapy). Preferably, said reagent comprises a peptide or a fusion protein as defined above, which has been labeled and/or complexed with an HLA molecule, in the form of multimeric HLA/peptide complexes, for instance tetramers of HLA/peptide complexes, which have been labeled.

A subject of the present invention is also an in vitro method for immunomonitoring the cellular response against cyclin B1 in an individual who has cancer, characterized in that it comprises:

bringing a biological sample from said individual into contact with a peptide comprising at least one cyclin B1 CD4$^+$ T epitope which is immunodominant in vitro, or a peptide derivative of said peptide as defined above, and detecting cyclin-B1-specific CD4$^+$ T lymphocytes by any appropriate means.

The method according to the invention makes it possible to monitor the evolution of the CD4$^+$ T response directed against cyclin B1 during cancer or else during an antitumor treatment, in particular an antitumor immunotherapy; the cyclin-B1-specific CD4$^+$ T lymphocytes may be of TH1 type (secretion of IFN-γ), TH2 type (secretion of IL-4) or regulatory T type (secretion of IL-10 or of TGF-β); the TH1-type T response is expected to be a sign of a favorable evolution for the patent, whereas the regulatory T response is expected to be a sign of an unfavorable evolution for the patient. The detection is carried out using a biological sample containing CD4$^+$ T cells, in particular a sample of mononuclear cells isolated from a peripheral blood sample (PBMCs). This method is carried out according to the conventional techniques known to those skilled in the art, as described in particular in international application WO 2009/153463 (page 23, line 20 to page 26, line 14).

A subject of the present invention is also an immunomonitoring reagent comprising at least one peptide/peptide derivative as defined above. Preferably, said reagent is included in a kit. Said immunomonitoring reagent advantageously comprises a peptide, polypeptide or fusion protein as defined above, which has optionally been labeled or complexed, in particular complexed with labeled, for example biotinylated, HLA molecules, in the form of multimeric HLA/peptide complexes, for instance tetramers of HLA/peptide complexes, which have been labeled.

A subject of the present invention is thus also a method for analyzing cyclin-B1-specific CD4+ T lymphocytes, characterized in that it comprises at least the following steps:

bringing a cell sample into contact, in vitro, with multimeric HLA/peptide complexes which have been labeled, in particular with a fluorochrome, said complexes being formed by the binding of soluble HLA molecules with at least one peptide/peptide derivative as defined above, and analyzing the cells bound to said HLA/peptide complexes, in particular by flow cytometry.

According to one advantageous embodiment of said method, the analysis of the cells (CD4+ T lymphocytes) comprises sorting said cells.

A subject of the present invention is also a peptide comprising a cyclin B1 CD4+ T epitope, capable of binding to 3 to 5 or at least 6 different predominant HLA II molecules as defined above, with the exception of the peptides 212-226, 216-230 and 221-235, and also a derived modified peptide, polynucleotide, vector, host cell and immunogenic or vaccine composition.

The polynucleotides, the recombinant vectors and the transformed cells as defined above are of use in particular for the production of the peptides, polypeptides and fusion proteins according to the invention.

The polynucleotides according to the invention are obtained by conventional methods, known in themselves, according to standard protocols such as those described in *Current Protocols in Molecular Biology* (Frederick M AUSUBEL, 2000, Wiley and son Inc, Library of Congress, USA). For example, they can be obtained by amplification of a nucleic sequence by PCR or RT-PCR, by screening of genomic DNA libraries by hybridization with a homologous probe, or else by total or partial chemical synthesis. The recombinant vectors are constructed and introduced into host cells by conventional recombinant DNA and genetic engineering methods, which are known in themselves.

The peptides and derivatives thereof as defined above are prepared by conventional techniques known to those skilled in the art, in particular by solid-phase or liquid-phase synthesis or by expression of a recombinant DNA in an appropriate (eukaryotic or prokaryotic) cell system.

More specifically:

the peptides and derivatives thereof (variants, multi-epitope polypeptides) can be solid-phase synthesized according to the Fmoc technique, originally described by Merrifield et al. (J. Am. Chem. Soc., 1964, 85: 2149-) and purified by reverse-phase high performance liquid chromatography, the lipopeptides can in particular be prepared according to the process described in international application WO 99/40113 or WO 99/51630, the peptides and derivatives such as the variants, the multi-epitope polypeptides and fusion proteins can also be produced from the corresponding cDNAs, obtained by any means known to those skilled in the art; the cDNA is cloned in a eukaryotic or prokaryotic expression vector and the protein or the fragment produced in the cells modified by the recombinant vector are purified by any appropriate means, in particular by affinity chromatography.

Figure 2:
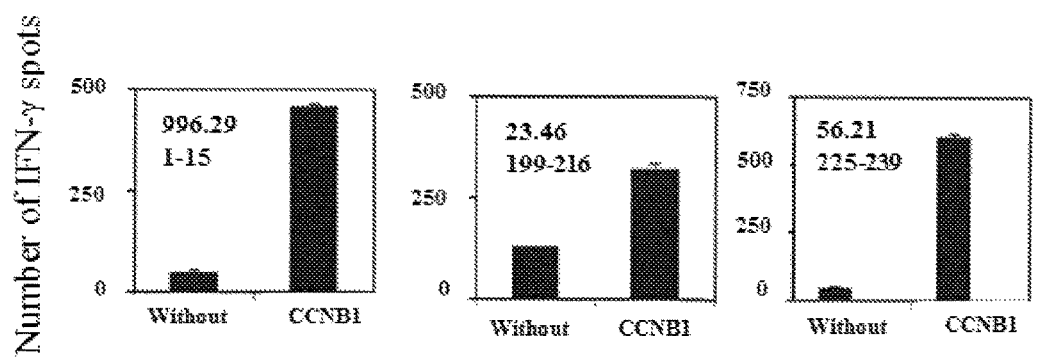

In addition to the above arrangements, the invention also comprises other arrangements, which will emerge from the description which follows, which refers to examples of implementation of the subject of the present invention, with reference to the appended drawings in which:

FIG. 1 illustrates the specificity and the magnitude of the response of CD4+ T lymphocytes with respect to CCNB1. The CD4+ T lymphocyte lines were obtained by in vitro stimulation with autologous dendritic cells pre-loaded with the CCNB1 protein. A. Examples of CD4+ T lymphocyte lines specific for CCNB1 peptides. B. Frequencies of CD4+ T lymphocytes specific for KLH and for CCNB1 in donor blood;

FIG. 2 illustrates the recognition of the CCNB1 protein by the CD4+ T lymphocyte lines directed against the peptides. The CD4+ T lymphocyte lines were obtained by in vitro stimulation with autologous dendritic cells pre-loaded with CCNB1 peptides. The CD4+ T lymphocyte lines were brought into contact with autologous dendritic cells pre-loaded with CCNB1 and the activation thereof was tested by IFN-gamma Elispot after 24 h of incubation. A. Examples of CCNB1-peptide-specific CD4+ T lymphocyte lines recognizing CCNB1. The name of the CD4+ T lymphocyte line and its peptide specificity are indicated in the quadrant. B. Number of peptide-specific CD4+ T lymphocyte lines recognizing CCNB1.

EXAMPLE 1: MATERIALS AND METHODS

1) Peptide Synthesis

The peptides were synthesized according to the Fmoc strategy in solid-phase parallel synthesis by means of a resin of Rink amide type, purified by HPLC and controlled by mass spectrometry (ES-MS). The N-terminal of all the peptides is free and the C-terminal of all the peptides is amidated.

2) Production and Purification of the Recombinant Human CCNB1 Protein

*E. coli* bacteria of the BL 21 strain were transformed by electroporation (2500 V, 4.8 ms) with the pET-28a-(+) plasmid (Novagen) into which the human CCNB1 gene had been cloned. After preculture in LB medium for 20 min at 37° C., the transformed bacteria were cultured for 48 h at 37° C. in LB/kanamycin selective medium, and then expression of cyclin B1 was induced by incubation for 21 h at 15° C. in the presence of IPTG. The protein produced, which has a His tag, was extracted from the bacteria by cell lysis (treatment with lysozymes followed by mechanical grinding and then a treatment with benzonases), and then purified by several successive chromatography operations: a step of affinity chromatography on a HisTrap column (nickel column, GE Healthcare), a step of exclusion chromatography on a Superdex 75 column (GE Healthcare), a step of ion exchange chromatography on a HiTrap SP HP column (GE Healthcare), and a step of removal of the endotoxins by affinity chromatography on an EndoTrap Blue column (Lonza). The concentration of the protein in the final solution was determined by measuring the absorbance at 280 nm, and its purity was verified by mass spectrometry.

3) Cell Preparation

The blood samples (buffy coat) come from the Etablissement Francais du Sang [French blood bank] (Rungis center). The peripheral blood mononuclear cells (PBMCs) were isolated by means of a ficoll gradient. The immature dendritic cells (DCs) were obtained from the PBMCs by differentiation of the adherent cells after 5 days of culture in AIM-V medium (Life Technologies) containing 1000 U/ml of IL-4 and 1000 U/ml of GM-CSF (R&D Systems). The mature DCs were obtained from the immature DCs after having been cultured for two days in the presence of lipopolysaccharide (LPS). The CD4+ T lymphocytes were purified from the PBMCs using magnetic microbeads coupled to anti-CD4 antibodies (Miltenyi Biotec). The HLA-DRB1 genotyping of the donors was carried out by sequence-specific PCR using the All Set+™ Gold SSP HLA-DRB1 kit (Invitrogen).

4) Production of CD4+ T Lymphocyte Lines Specific for CCNB1 or for the Peptides

The CD4+ T lymphocytes (1 to $3\times10^5$) were cultured in round-bottomed 96-well plates with autologous immature DCs preloaded with 1.2 µM of CCNB1 and matured in the presence of LPS, or with autologous mature DCs preloaded with pools of peptides (10 µg/ml). The culturing is carried out in IMDM medium (Life Technologies) supplemented with human serum of group AB (complete IMDM medium) containing 1000 U/ml of IL-6 (R&D Systems) and 10 ng/ml of IL-12 (R&D Systems). The culture is stimulated at the end of one week by adding 10 000 to 30 000 DCs loaded with the CCNB1 protein or the pools of peptides, 20 U/ml of IL-2 (R&D Systems) and 10 ng/ml of IL-7 (R&D Systems). Another stimulation is carried out after 14 and optionally 21 days of culture. Between 5 and 7 days after the final stimulation, a specificity test is carried out by EliSpot. Each culture well constitutes a CD4+ T lymphocyte line.

5) Evaluation of the Specificity of CD4+ T Lymphocytes Cultured with CCNB1 or Peptides by EliSpot The anti-human IFN-γ antibody 1-D1K (Mabtech) is adsorbed at 2.5 µg/ml in 1×PBS onto 96-well Multiscreen®-HA plates (Millipore) by overnight incubation at 4° C. The plates are then saturated by incubation for 2 hours at 37° C. with complete IMDM medium. The CD4+ T lymphocytes are incubated for 16 hours at 37° C. in these plates after having been washed in AIM-V/IL-7 medium (0.5 ng/ml of IL-7). The autologous immature DCs (5000 cells/well) preloaded for 4 hours with the CCNB1 protein or KLH (0.5 to 3 µM) or PBMCs (50 000 cells/well) incubated in the presence of 10 µg/ml of peptides are used as presenting cells. After incubation, the plates are washed with distilled water, PBS/0.05% Tween and PBS. 100 µl/well of biotinylated anti-human IFN-γ Ab 7-B6-1 (Mabtech) at 0.25 µg/ml in 1×PBS/1% BSA is added to the plates, which are incubated for 1 h 30 min at 37° C. After several washes in PBS or PBS/0.05% tween, the IFN-γ secretion is demonstrated by adding extravidin-alkaline phosphatase (Sigma) and NBT/BCIP. After 5 to 10 minutes of incubation, the reaction is stopped by washing with running water. After drying, the spots are counted on an Elispot reader (AID). A CD4+ T lymphocyte line is considered to be antigen-specific if the number of spots in the wells containing the antigen is at least two times higher than the well not containing the antigen, the difference between the 2 types of well being at least greater than 25. The frequency of the CD4+ T lymphocytes present in the donor blood is estimated using the Poisson's law distribution according to the formula: frequency=−Ln ((number of nonspecific lines/total number of lines tested))/(number of CD4+ lymphocytes incubated in each well).

6) Purification of Class II HLA Molecules

Lymphoblastoid cells transformed with the EBV virus, homozygous for class II HLA molecules, are used as a source of class II HLA molecules (Texier et al., J. Immunol., 2000, 164, 3177-3184; Texier et al., Eur. J. Immunol., 2001, 31, 1837-1846; Castelli et al., J. Immunol., 2002, 169, 6928-6934). The HLA-DR and HLA-DP molecules are purified by affinity chromatography by means of the L243 anti-HLA-DR (ATCC, Rockville, USA) and B7/21 anti-HLA-DP monoclonal antibodies coupled to a protein A sepharose CL 4B gel (Pharmacia).

7) Measurement of the Relative Affinity of the Peptides for the Class II HLA Molecules The affinity of the peptides is evaluated by competition between a biotinylated peptide and the test peptide with respect to the class II HLA molecules. Complexes are revealed by ELISA. These tests are described in American patent U.S. Pat. No. 6,649,166 and PCT international application WO 03/040299, respectively for the HLA-DR and HLA-DP4 molecules. The use of these tests to measure the activity with respect to binding of peptides derived from various antigens is illustrated in American patent U.S. Pat. No. 6,649,166 and PCT international applications WO 02/090382, WO 03/040299 and WO 2004/014936.

More specifically, the class II HLA molecules are diluted in a 10 mM phosphate buffer containing 150 mM NaCl, 1 mM dodecylmaltoside (DM) and 10 mM citrate with a fixed concentration of the biotinylated peptide and dilutions of the test peptide. The plates are incubated for 24 h to 72 h. After neutralization with 50 µl of 450 mM Tris-HCl buffer, pH=7.5, containing 0.003% thimerosal, 0.3% BSA and 1 mM DM, the samples are transferred onto 96-well ELISA plates (Maxisorp®, Nunc), onto which the L243 (anti-HLA-DR) or B7/21 (anti-HLA-DP) antibodies have been adsorbed at a concentration of 10 µg/ml. These plates were also saturated with a 100 mM Tris-HCl buffer, pH=7.5, containing 0.3% BSA and 0.003% thimerosal. After 2 hours of incubation, the ELISA plates are washed. The presence of the biotinylated peptide in the wells is revealed by successive incubation of a streptavidin-alkaline phosphatase conjugate (GE Healthcare) and of 4-methylumbelliferyl phosphate as substrate (Sigma). The fluorescence emitted is measured at 450 nm after excitation at 365 nm by means of a Gemini spectrofluorimeter (Molecular Devices). The maximum binding is given by the wells not containing competitor, and the background noise is measured in the wells not containing HLA molecule. For each peptide, the concentration inhibiting 50% of the maximum binding (IC50) is evaluated. Each experiment is controlled using a reference peptide which is the non-biotinylated form of the tracer peptide. Their sequence and their IC50 value are the following: HA 306-318 (PKYVKQNTLKLAT; SEQ ID No. 2) for DRB1*01:01 (1 nM), DRB1*04:01 (6 nM), DRB1*11:01 (5 nM) and DRB5*01:01 (3 nM), YKL (AAYAAAKAAALAA; SEQ ID No. 3) for DRB1*07:01 (10 nM), A3 152-166 (EAEQLRAYLDGTGVE; SEQ ID No. 4) for DRB1*15:01 (30 nM), MT 2-16 (AKTIAYDEE-ARRGLE; SEQ ID No. 5) for DRB1*03:01 (121 nM), B1 21-36 (TERVRLVTRHIYNREE; SEQ ID No. 6) for DRB1*13:01 (51 nM), LOL 191-210 (ESWGAVWRIDTP-DKLTGPFT; SEQ ID No. 7) for DRB3*01:01 (28 nM), E2/E168 (AGDLLAIETDKATI; SEQ ID No. 8) for DRB4*01:01 (10 nM) and Oxy 271-287 (EKKYFAATQFE-PLAARL; SEQ ID No. 9) for DPB1*04:01 (7 nM) and DPB1*04:02 (6 nM). The data are expressed in the form of relative affinity: IC50 of the peptide/IC50 of the reference peptide. A relative affinity value of less than 100 corresponds to a peptide which is a ligand of the class II HLA molecule. Each value is the average of at least two independent experiments.

EXAMPLE 2: CHOICE OF THE SEQUENCE OF THE CNBB1 PEPTIDES

The class II HLA molecules and in particular the HLA-DR and HLA-DP molecules bind the antigenic peptides via several anchoring residues present on the sequence of the peptides. These peptides have a hydrophobic or aromatic residue in their N-terminal portion which constitutes the main anchoring residue, housed in the pocket P1 of the class II HLA molecule. In order to optimize the binding of the peptides to the class II HLA molecules, the overlaps of the peptides which cover the entire CCNB1 sequence were chosen in such a way that they all have a hydrophobic or aromatic residue in their N-terminal portion. These peptides, the sequence of which is presented in Table III, were synthesized.

TABLE III

Overlapping peptides derived from the CCNB1 protein (SEQ ID Nos. 10 to 84)

| Numbering* | Sequence |
|---|---|
| 1-15 | MALRVTRNSKINAEN |
| 9-23 | SKINAENKAKINMAG |
| 17-31 | AKINMAGAKRVPTAP |
| 25-39 | KRVPTAPAATSKPGL |
| 37-51 | PGLRPRTALGDIGNK |
| 43-57 | TALGDIGNKVSEQLQ |
| 50-64 | NKVSEQLQAKMPMKK |
| 54-68 | EQLQAKMPMKKEAKP |
| 58-72 | AKMPMKKEAKPSATG |
| 71-85 | TGKVIDKKLPKPLEK |
| 77-91 | KKLPKPLEKVPMLVP |
| 81-95 | KPLEKVPMLVPVPVS |
| 87-101 | PMLVPVPVSEPVPEP |
| 96-110 | EPVPEPEPEPEPEPV |
| 108-122 | EPVKEEKLSPEPILV |
| 113-127 | EKLSPEPILVDTASP |
| 118-132 | EPILVDTASPSPMET |
| 128-142 | SPMETSGCAPAEEDL |
| 140-154 | EDLCQAFSDVILAVN |
| 144-158 | QAFSDVILAVNDVDA |
| 147-161 | SDVILAVNDVDAEDG |
| 151-165 | LAVNDVDAEDGADPN |
| 164-178 | PNLCSEYVKDIYAYL |
| 168-182 | SEYVKDIYAYLRQLE |
| 172-186 | KDIYAYLRQLEEEQA |
| 179-193 | RQLEEEQAVRPKYLL |
| 185-199 | QAVRPKYLLGREVTG |
| 189-203 | PKYLLGREVTGNMRA |
| 195-209 | REVTGNMRAILIDWL |
| 199-213 | GNMRAILIDWLVQVQ |
| 202-216 | RAILIDWLVQVQMKF |
| 207-221 | DWLVQVQMKFRLLQE |
| 212-226 | VQMKFRLLQETMYMT |

TABLE III-continued

Overlapping peptides derived from the CCNB1 protein (SEQ ID Nos. 10 to 84)

| Numbering* | Sequence |
|---|---|
| 216-230 | FRLLQETMYMTVSII |
| 221-235 | ETMYMTVSIIDRFMQ |
| 225-239 | MTVSIIDRFMQNNCV |
| 231-245 | DRFMQNNCVPKKMLQ |
| 237-251 | NCVPKKMLQLVGVTA |
| 241-255 | KKMLQLVGVTAMFIA |
| 244-258 | LQLVGVTAMFIASKY |
| 250-264 | TAMFIASKYEEMYPP |
| 256-270 | SKYEEMYPPEIGDFA |
| 260-274 | EMYPPEIGDFAFVTD |
| 264-278 | PEIGDFAFVTDNTYT |
| 267-281 | GDFAFVTDNTYTKHQ |
| 269-283 | FAFVTDNTYTKHQIR |
| 275-289 | NTYTKHQIRQMEMKI |
| 280-294 | HQIRQMEMKILRALN |
| 285-299 | MEMKILRALNFGLGR |
| 291-305 | RALNFGLGRPLPLHF |
| 299-313 | RPLPLHFLRRASKIG |
| 303-317 | LHFLRRASKIGEVDV |
| 310-324 | SKIGEVDVEQHTLAK |
| 315-329 | VDVEQHTLAKYLMEL |
| 320-334 | HTLAKYLMELTMLDY |
| 323-337 | AKYLMELTMLDYDMV |
| 327-341 | MELTMLDYDMVHFPP |
| 332-346 | LDYDMVHFPPSQIAA |
| 338-352 | HFPPSQIAAGAFCLA |
| 342-356 | SQIAAGAFCLALKIL |
| 347-361 | GAFCLALKILDNGEW |
| 351-365 | LALKILDNGEWTPTL |
| 359-373 | GEWTPTLQHYLSYTE |
| 363-377 | PTLQHYLSYTEESLL |
| 366-380 | QHYLSYTEESLLPVM |
| 369-383 | LSYTEESLLPVMQHL |
| 374-388 | ESLLPVMQHLAKNVV |
| 377-391 | LPVMQHLAKNVVMVN |
| 385-399 | KNVVNVNQGITKHMT |
| 392-406 | QGLTKHMTVKNKYAT |

TABLE III-continued

Overlapping peptides derived from the CCNB1 protein
(SEQ ID Nos. 10 to 84)

| Numbering* | Sequence |
|---|---|
| 396-410 | KHMTVKNKYATSKHA |
| 402-416 | NKYATSKHAKISTLP |
| 410-424 | AKISTLPQLNSALVQ |
| 416-430 | PQLNSALVQDLAKAV |

*the numbering is done with reference to the human CNBB1 sequence (SEQ ID No. 1)
**the hydrophobic or aromatic residue is in bold

EXAMPLE 3: PRODUCTION OF CCNB1-PROTEIN-SPECIFIC CD4+ T LYMPHOCYTE LINES 8 healthy donors comprising HLA molecules which are varied and most of which are very frequent in the Caucasian population were selected. CD4+ T lymphocyte lines were obtained by coculture of the CD4+ T lymphocytes with autologous dendritic cells preloaded with the CCNB1 protein, produced recombinantly in E. coli. At the end of the culture, each line was tested by Elispot for its capacity to recognize pools of peptides which cover the sequence of the CCNB1 protein, and then, in a second test, the individual peptides contained in the pool recognized by the lines. In order to be sure that each donor had the capacity to respond, KLH-specific CD4+ T lymphocyte lines were also produced.

Table IV indicates the peptides recognized by the cyclin-B1-specific CD4+ T lymphocytes and the number of specific lines which are associated therewith.

Acad. Sci. USA, 2009, 106, 14010-14015; application US 2011/0280897). In addition, the identified peptides participate in the response against CCNB1, given that the CD4+ T lymphocytes were generated by stimulation with the CCNB1 protein. Examples of a line of CD4+ T lymphocytes specific for CCNB1 and for peptides of this protein are presented (FIG. 1A).

On the basis of the number of lines obtained, the frequency of the CD4+ T lymphocytes pre-existing in the blood of the donors was evaluated. For these 8 donors, this average frequency is 0.82 for CCNB1 and at least 9.2 for KLH, all the donors being responders to the 2 proteins (FIG. 1B). This precursor frequency value corresponds to immunogenic proteins (Delluc et al., Blood, 2010, 116, 4542-4545; Delluc et al., Faseb J., 2011, 25, 2040-2048).

EXAMPLE 4: AFFINITY OF THE CCNB1 PEPTIDES FOR THE CLASS II HLA MOLECULES

All of the overlapping peptides covering the cyclin B1 sequence were tested for their capacity to bind to class II HLA molecules by means of a competitive binding assay as described in Example 1. The data are presented in 3 different tables according to the peptides: the peptides having been found to be of the CCNB1 T epitopes which are immunodominant in vitro during the previous experiments (Table V), the additional peptides having a broad binding specificity with respect to class II HLA molecules (Table VI), and the rest of the peptides (Table VII). For each peptide, the concentration inhibiting 50% of the maximum binding (IC50) is evaluated. The data are expressed in the form of

TABLE IV

Peptide specificity of the CCNB1-specific T lymphocyte lines

| Donors | Typing HLA-DRB1 | peptides | | | | | | | | | | | | | | | TOTAL |
|---|---|---|---|---|---|---|---|---|---|---|---|---|---|---|---|---|---|
| | | 1-15 | 17-31 | 25-39 | 118-132 | 280-294 | 285-299 | 303-317 | 315-329 | 320-334 | 323-337 | 374-388 | 377-391 | 410-424 | 416-430 | 419-433 | |
| 693 | 01:02/13:01 | | | | | | 3 | 1 | | | | | | | | | 4 |
| 694 | 04:01/15:01 | | | 1 | | | 1 | | | 1 | | | | | 1 | | 4 |
| 703 | 07:01/13:02 | | | | 1 | 2 | | | | | | | | | | | 3 |
| 721 | 03:01/11:01 | | | | | | | | | | | | | 2 | | | 2 |
| 593 | 01:01/08:01 | | | | | | 1 | | 1 | 1 | | | | | | | 3 |
| 784 | 07:01/11:01 | 2 | 1 | 1 | | | | | | | | | | | | 5 | 9 |
| 795 | 11:01/15:01 | | | | | | | | | | | | | | 1 | | 1 |
| 803 | 04:04/04:01 | 2 | | | | | | | | | 1 | 1 | | | | | 4 |
| Total | | 4 | 1 | 1 | 1 | 1 | 7 | 1 | 1 | 1 | 1 | 1 | 1 | 3 | 1 | 5 | |

15 different peptides corresponding to CCNB1 CD4+ T epitopes which are immunodominant in vitro were identified (Table IV). 3 peptides are common to at least two individuals (Table IV). These 15 T epitopes which are immunodominant in vitro are different than the known T epitopes (epitopes 215-229, 219-233 and 223-234; Vella et al., Proc. Natl. Acad. Sci. USA, 2009, 106, 14010-14015; application US 2011/0280897) and are located outside the corresponding region of CNBB1 (region 215-233; Vella et al., Proc. Natl.

relative affinity: IC50 of the peptide/IC50 of the reference peptide. A relative affinity value of less than 100 corresponds to a peptide which is a ligand of the class II HLA molecule. A relative affinity value of less than 20 corresponds to a peptide which has a strong affinity (value in bold). Each value is the average of at least two independent experiments. The peptides in bold were selected for the subsequent experiments.

TABLE V

Class II HLA molecule-binding activity of the T epitopes which are immunodominant in vitro

| Peptides | DR1 | DR3 | DR4 | DR7 | DR11 | DR13 | DR15 |
|---|---|---|---|---|---|---|---|
| 1-15 | 100 | >825 | 46 | 2 | 22 | 58 | 5 |
| 17-31 | 5 | 833 | >1771 | 3 | 2 | 21 | 120 |
| 280-294 | 1225 | 0.2 | 0.4 | 462 | 2000 | >1949 | 0.3 |
| 285-299 | 1 | 51 | 7 | 0.1 | 4 | 1 | 0.03 |
| 303-317 | 495 | 3 | 1394 | 849 | 1 | 1 | 17 |
| 320-334 | 16 | 1 | 1 | 18 | 2 | 10 | 3 |
| 323-337 | 4 | 2 | 0.2 | 8 | 0.4 | >1 949 | 2 |
| 374-388 | 837 | 764 | 91 | 3 | 0.3 | 6 | 19 |
| 410-424 | 89 | >825 | 408 | >1036 | 1 | 94 | 12 |
| 416-430 | 693 | 9 | 54 | 47 | 123 | >1949 | 71 |
| 419-433 | 155 | 1 | 333 | 183 | 3 | 37 | 7 |
| 25-39 | >11 262 | >825 | >1771 | >1036 | >1949 | >1949 | >329 |
| 118-132 | 6359 | 0.4 | 0.3 | >1036 | >1949 | >1949 | 400 |
| 315-329 | 2449 | >825 | 149 | 6 | 632 | 211 | 7 |
| 377-391 | 894 | 177 | 373 | 13 | 3 | 2 | >329 |

| Peptides | DRB3 | DRB4 | DRB5 | DP401 | DP402 | Number HLA II |
|---|---|---|---|---|---|---|
| 1-15 | >362 | >961 | 374 | >1357 | >1733 | 6 |
| 17-31 | >362 | >961 | 11 | >1357 | >1733 | 5 |
| 280-294 | 53 | >961 | 4 | >1357 | >1733 | 5 |
| 285-299 | >362 | 18 | 2 | 30 | 4 | 11 |
| 303-317 | >362 | >961 | 1333 | >1357 | >1733 | 4 |
| 320-334 | 24 | 18 | 17 | 8 | 3 | 12 |
| 323-337 | 41 | 7 | 2 | 1 | 6 | 11 |
| 374-388 | >362 | 424 | 91 | >1357 | >1733 | 6 |
| 410-424 | >362 | 966 | >3467 | >1357 | 1118 | 4 |
| 416-430 | 3 | 1800 | 548 | 59 | 74 | 7 |
| 419-433 | 7 | >961 | 112 | >1357 | 148 | 5 |
| 25-39 | >362 | >961 | >3467 | >1357 | >1733 | 0 |
| 118-132 | 12 | >961 | >3467 | >1357 | >1733 | 3 |
| 315-329 | >362 | >961 | 224 | >1357 | >1733 | 2 |
| 377-391 | >362 | >961 | 4082 | >1357 | >1733 | 3 |

Table V shows that, out of the 15 peptides identified as being immunodominant in vitro, 11 peptides bind to at least 4 different class II HLA molecules, 3 peptides binding to more than 11 molecules out of the 12 tested.

Table VI presents the results of other peptides which also have a broad class II HLA molecule-binding specificity. These peptides bind to at least 6 different molecules.

TABLE VI

Class II HLA molecule-binding activity of peptides other than the peptides which are immunodominant in vitro, said other peptides having a broad binding specificity

| peptides | DR1 | DR3 | DR4 | DR7 | DR11 | DR13 | DR15 | DRB3 | DRB4 | DRB5 | DP401 | DP402 | Number HLA II |
|---|---|---|---|---|---|---|---|---|---|---|---|---|---|
| 168-182 | 22 | 97 | 163 | 346 | 3 | 12 | 12 | 30 | >961 | 3 | 159 | 127 | 7 |
| 199-213 | 27 | 1 | 56 | 10 | 77 | >1 949 | 1 | 9 | 9 | 58 | 36 | 24 | 11 |
| 202-216 | 1 225 | 1 | 59 | 9 | 400 | >1 949 | 4 | 2 | 20 | 55 | 47 | 14 | 9 |
| 207-221 | 38 | 0.5 | >1771 | 7 | 0.4 | 1 | 7 | 160 | 49 | 5 | >1357 | 171 | 8 |
| 212-226 | 1 | 1 | 2 | 40 | 5 | 1 | 46 | 34 | 683 | 2 | 110 | 9 | 10 |
| 216-230 | 7 | 1 | 2 | 0.5 | 14 | >1949 | 3 | 11 | 22 | 50 | 2 | 1 | 11 |
| 221-235 | 89 | 0.5 | 37 | 1 | 1 | 59 | 0.3 | 22 | 7 | 1 | 59 | 68 | 12 |
| 225-239 | 24 | 1 | 100 | 5 | 31 | >1949 | 2 | 9 | 6 | 79 | 72 | 35 | 11 |
| 241-255 | 3 | 15 | 1 | 0.1 | 90 | >1949 | 1 | >362 | 141 | 1 | 424 | 35 | 8 |
| 244-258 | 2 | 9 | 141 | 1 | 23 | >1949 | 1 | 267 | 98 | 1 | 77 | 32 | 9 |
| 250-264 | 22 | 4 | 70 | 4 | 6 | 3 | 9 | 34 | >961 | 82 | 0.1 | 1 | 11 |
| 267-281 | 1500 | 0.2 | 1 | 22 | 1333 | 62 | 86 | 38 | >961 | 24 | >1357 | >1733 | 7 |
| 299-313 | 63 | 168 | 624 | 35 | 0.1 | 0.2 | 200 | >362 | 13 | 26 | >1357 | >1733 | 6 |
| 342-356 | 46 | >825 | 163 | 20 | 3 | >1949 | 21 | 239 | 57 | 163 | 79 | 25 | 7 |
| 363-377 | 28 | 1 | 76 | 1 | 45 | >1949 | 1 | 11 | 5 | 24 | 22 | 50 | 11 |
| 366-380 | 32 | 119 | 65 | 1 | 55 | >1949 | 47 | 32 | >961 | 471 | 0.2 | 0.3 | 8 |

Table VII presents the results of the remaining peptides.

TABLE VII

Class II HLA molecule-binding activity of the rest of the peptides covering cyclin B1

| peptides | DR1 | DR3 | DR4 | DR7 | DR11 | DR13 | DR15 | DRB3 | DRB4 | DRB5 | DP401 | DP402 | Number HLA II |
|---|---|---|---|---|---|---|---|---|---|---|---|---|---|
| 9-23 | >11 262 | 22 | >1 771 | >1 036 | 490 | 146 | >329 | >362 | >961 | 1000 | >1 357 | >1 733 | 1 |
| 37-51 | >11 262 | >825 | >1 771 | >1 036 | >1 949 | 422 | >329 | >362 | >961 | >3 467 | >1 357 | >1 733 | 0 |
| 43-57 | >11 262 | >825 | >1 771 | >1 036 | >1 949 | 1 789 | 300 | >362 | >961 | >3 467 | >1 357 | >1 733 | 0 |
| 50-64 | >11 262 | >825 | >1 771 | >1 036 | 1549 | 258 | >329 | >362 | >961 | 51 | >1 357 | >1 733 | 1 |
| 54-68 | 3742 | >825 | >1 771 | 808 | 1414 | 105 | >329 | >362 | >961 | 35 | >1 357 | >1 733 | 1 |
| 58-72 | >11 262 | >825 | >1 771 | >1 036 | 40 | 683 | >329 | >362 | >961 | >3 467 | >1 357 | >1 733 | 1 |
| 71-85 | >11 262 | 228 | >1 771 | >1 036 | >1 949 | >1 949 | >329 | >362 | >961 | 250 | >1 357 | >1 733 | 0 |
| 77-91 | >11 262 | >825 | >1 771 | >1 036 | 1633 | >1 949 | >329 | >362 | 75 | >3 467 | 212 | 474 | 1 |
| 81-95 | 524 | >825 | 500 | >1 036 | >1 949 | >1 949 | >329 | >362 | 141 | >3 467 | >1 357 | >1 733 | 0 |
| 87-101 | 1500 | >825 | 96 | 231 | >1 949 | >1 949 | 134 | >362 | 748 | >3 467 | >1 357 | >1 733 | 1 |
| 96-110 | >11 262 | >825 | >1 771 | >1 036 | >1 949 | >1 949 | >329 | >362 | >961 | >3 467 | >1 357 | >1 733 | 0 |
| 108-122 | 894 | >825 | >1 771 | >1 036 | >1 949 | >1 949 | >329 | >362 | >961 | >3 467 | >1 357 | >1 733 | 0 |
| 113-127 | 6000 | 6 | 55 | >1 036 | >1 949 | >1 949 | >329 | 151 | 231 | >3 467 | 72 | 71 | 4 |
| 128-142 | 3586 | >825 | >1 771 | >1 036 | >1 949 | >1 949 | >329 | >362 | >961 | >3 467 | >1 357 | >1 733 | 0 |
| 140-154 | >11 262 | 161 | 1107 | >1 036 | >1 949 | >1 949 | 207 | >362 | >961 | >3 467 | >1 357 | >1 733 | 0 |
| 144-158 | 1 732 | 8 | 12 | >1 036 | >1 949 | >1 949 | 46 | 18 | >961 | >3 467 | 51 | 129 | 5 |
| 147-161 | >11 262 | >825 | 54 | >1 036 | >1 949 | >1 949 | 7 | >362 | >961 | >3 467 | >1 357 | >1 733 | 2 |
| 151-165 | >11 262 | >825 | 667 | >1 036 | >1 949 | >1 949 | >329 | >362 | >961 | >3 467 | >1 357 | >1 733 | 0 |
| 164-178 | 2828 | >825 | 527 | 73 | >1 949 | >1 949 | 28 | 53 | 40 | 500 | 274 | 625 | 4 |
| 172-186 | 42 | 33 | 187 | 1 600 | 1 | 5 | 11 | >362 | >961 | 775 | >1 357 | >1 733 | 5 |
| 179-193 | 9000 | >825 | >1 771 | 271 | >1 949 | 943 | >329 | >362 | >961 | 2 160 | >1 357 | >1 733 | 0 |
| 185-199 | 59 | >825 | 260 | >1 036 | 22 | 4 | >329 | >362 | >961 | 1 667 | >1 357 | >1 733 | 3 |
| 189-203 | 17 | 764 | 34 | >1 036 | 3 | >1 949 | >329 | >362 | >961 | 129 | >1 357 | >1 733 | 3 |
| 195-209 | 55 | 1 | 260 | 173 | 1183 | 45 | 30 | 20 | 23 | 1 414 | 725 | 791 | 5 |
| 231-245 | 11 | >825 | 52 | >1 036 | 2 000 | >1 949 | >329 | >362 | >961 | 1 581 | >1 357 | >1 733 | 2 |
| 237-251 | 4 | >825 | 179 | 115 | 87 | >1 949 | 65 | >362 | 1 400 | 112 | >1 357 | >1 733 | 3 |
| 256-270 | 3 | >825 | 456 | 61 | 1366 | >1 949 | 153 | >362 | >961 | 603 | 894 | >1 733 | 2 |
| 264-278 | 7000 | 85 | 2 | 86 | 1667 | >1 949 | 300 | 19 | >961 | 61 | >1 357 | >1 733 | 5 |
| 269-283 | 1342 | 0.1 | 0.4 | 577 | 2191 | >1 949 | 17 | 34 | >961 | 42 | >1 357 | >1 733 | 5 |
| 275-289 | 173 | >825 | 456 | 43 | 4 | 158 | 85 | >362 | 80 | 50 | >1 357 | >1 733 | 5 |
| 291-305 | 1 | >825 | 1 414 | 3 | 1000 | >1 949 | 65 | >362 | >961 | 4 | >1 357 | >1 733 | 4 |
| 310-324 | >11 262 | 306 | >1 771 | >1 036 | 190 | 1800 | >329 | >362 | >961 | 1500 | >1 357 | >1 733 | 0 |
| 327-341 | 418 | 32 | 22 | 126 | 216 | >1 949 | 10 | >362 | 139 | 163 | 2 | 47 | 5 |
| 332-346 | 224 | >825 | 289 | 20 | 511 | >1 949 | 36 | >362 | >961 | 1 581 | >1 357 | >1 733 | 2 |
| 338-352 | 598 | >825 | >1 771 | 1400 | >1 949 | >1 949 | 257 | >362 | >961 | >3 467 | >1 357 | 188 | 0 |
| 347-361 | >11 262 | >825 | >1 771 | >1 036 | 9 | >1 949 | 1 | >362 | >961 | >3 467 | >1 357 | >1 733 | 2 |
| 351-365 | 648 | >825 | 1 000 | 624 | 2333 | >1 949 | 52 | >362 | >961 | 3055 | >1 357 | 510 | 2 |
| 359-373 | 548 | >825 | 500 | 0.4 | 22 | >1 949 | 0.2 | >362 | >961 | 224 | >1 357 | >1 733 | 3 |
| 369-383 | 212 | >825 | 58 | 91 | 45 | >1 949 | 350 | 72 | >961 | 1379 | 4 | 1 | 6 |
| 385-399 | 4500 | 228 | 986 | >1 036 | 766 | 37 | 0.02 | >362 | >961 | 52 | 116 | 2 | 4 |
| 392-406 | >11 262 | 408 | 577 | 533 | 693 | 7 | 129 | >362 | >961 | 47 | >1 357 | >1 733 | 2 |
| 396-410 | 7483 | >825 | 408 | 533 | 7 | 9 | 229 | >362 | >961 | 187 | >1 357 | >1 733 | 2 |
| 402-416 | 367 | >825 | 707 | 9 | 4 | >1 949 | >329 | >362 | >961 | 1 732 | >1 357 | >1 733 | 2 |

Some of the peptides of Table VII are capable of binding to 4 or 5 class II HLA molecules.

The peptides of Table VI and the 11 peptides which are immunodominant in vitro and bind to at least 4 different class II HLA molecules (Table V) were retained for additional studies. On the other hand, none of the peptides of Table VII was retained, since the number of peptides that could be evaluated was limited.

EXAMPLE 5: INDUCTION OF CD4+ T LYMPHOCYTE LINES SPECIFIC FOR CYCLIN B1 PEPTIDES

The peptides retained for the CD4+ T lymphocyte line induction tests are described in Table VIII. For 7 peptides, the overlapping sequences were combined with one another, forming longer peptides ranging up to 20 amino acids.

TABLE VIII

Sequences of the peptides tested for their capacity to induce specific CD4+ T lymphocytes

| Sequences | Combination | Sequence | SEQ ID NO: | Size |
|---|---|---|---|---|
| 1-15 | | MALRVTRNSKINAEN | 10 | 15 |
| 17-31 | | AKINMAGAKRVPTAP | 12 | 15 |
| 168-182 | | SEYVKDIYAYLRQLE | 33 | 15 |
| 199-216 | 199-213, 202-216 | GNMRAILIDWLVQVQMKF | 85 | 18 |
| 207-221 | | DWLVQVQMKFRLLQE | 41 | 15 |
| 212-226 | | VQMKFRLLQETMYMT | 42 | 15 |
| 216-230 | | FRLLQETMYMTVSII | 43 | 15 |
| 221-235 | | ETMYMTVSIIDRFMQ | 44 | 15 |
| 225-239 | 241-255, 244-258 | MTVSIIDRFMQNNCV | 45 | 15 |
| 241-258 | | KKMLQLVGVTAMFIASKY | 86 | 18 |
| 250-264 | | TAMFIASKYEEMYPP | 50 | 15 |
| 267-281 | 280-294, 285-299 | GDFAFVTDNTYTKHQ | 54 | 15 |
| 280-299 | 299-313, 303-317 | HQIRQMEMKILRALNFGLGR | 87 | 20 |
| 299-317 | 320-334, 323-337 | RPLPLHFLRRASKIGEVDV | 88 | 19 |
| 320-337 | | HTLAKYLMELTMLDYDMV | 89 | 18 |
| 342-356 | 363-377, 366-380 | SQIAAGAFCLALKIL | 69 | 15 |
| 363-380 | | PTLQHYLSYTEESLLPVM | 90 | 18 |
| 374-388 | | ESLLPVMQHLAKNVV | 76 | 15 |
| 410-424 | 416-430, 419-433 | AKISTLPQLNSALVQ | 85 | 15 |
| 416-433 | | PQLNSALVQDLAKAVAKV | 91 | 18 |

13 healthy donors comprising HLA molecules which are varied and most of which are very frequent in the Caucasian population were selected (Table IX).

CD4+ T lymphocyte lines were obtained by coculture of the CD4+ T lymphocytes with autologous dendritic cells preloaded with pools of peptides. After amplification of the T lymphocytes, each line was tested by Elispot (Table IX). The results are reported in the form of the number of times when a response to a peptide is observed. All the peptides induce a T lymphocyte response, but the strength of the response and the number of responders are very variable. 9 peptides activate T lymphocytes in more than half the donors.

However, notably, the most effective peptides, capable of inducing the most effective specific CD4+ T response (response strength greater than 2.5% and which can reach 6.1% and responder frequency greater than 65% and which can reach 85%) in a population of individuals carrying varied HLA II molecules, comprising all the HLA-DRB1 molecules that are the most frequent in the Caucasian population, covering by themselves 80% of the individuals of the Caucasian population, correspond to peptides which are immunodominant in vitro.

TABLE IX

Analysis of the average strength and the frequency of the CD4+ T response induced by the peptides

| | | Number of specific responses | | | | | | | | | | |
|---|---|---|---|---|---|---|---|---|---|---|---|---|
| Donor | HLA-DRB1 Typing | 1-15 | 17-31 | 168-182 | 199-216 | 207-221 | 212-226 | 216-230 | 221-235 | 225-239 | 241-258 | 250-264 |
| 877 | 01:01/13:01 | 1 | | 1 | | | | | | | 4 | 1 |
| 829 | 07:01/15:01 | | | | | | | | | 1 | 3 | |
| 876 | 11:01/11:04 | 3 | | | | | | | | | 1 | 2 |
| 996 | 08:04/14:08 | 2 | 5 | 2 | | 1 | | | | 1 | 1 | |
| 14 | 07:01/13:01 | 1 | 1 | 1 | 1 | | | | 2 | 1 | 1 | |
| 22 | 01:01/09:01 | 1 | 2 | 2 | | 1 | | | 3 | 1 | 3 | |

TABLE IX-continued

Analysis of the average strength and the frequency of the CD4+ T response induced by the peptides

| Donor | HLA-DRB1 Typing | | | | | | | | | | | |
|---|---|---|---|---|---|---|---|---|---|---|---|---|
| 23 | 04:01/13:01 | 1 | 1 | | 1 | | 1 | 1 | 1 | 1 | | |
| 26 | 11:04/15:01 | 4 | 3 | 1 | 2 | | | | | | | |
| 30 | 07:01/11:01 | 1 | | 1 | 1 | 2 | | 1 | 1 | | | |
| 32 | 03:01 | | | | | | | | | 1 | | |
| 62 | 01:01/04:05 | | | | | 1 | 3 | 4 | | 1 | 2 | |
| 31 | 13:01/16:01 | 1 | | 4 | | 1 | | 8 | 1 | | | |
| 56 | 07:01/11:01 | 3 | 2 | 1 | 3 | | 1 | 1 | 1 | 2 | | |
| | total | 18 | 14 | 13 | 8 | 6 | 5 | 15 | 10 | 8 | 15 | 3 |
| | Average strength (%) | 2.8 | 2.2 | 2.0 | 1.2 | 0.9 | 0.8 | 2.4 | 1.5 | 1.2 | 2.3 | 0.5 |
| | responders | 10 | 6 | 8 | 5 | 5 | 3 | 5 | 7 | 7 | 7 | 2 |
| | frequency | 77% | 46% | 62% | 38% | 38% | 23% | 38% | 54% | 54% | 54% | 15% |

| | | Number of specific responses | | | | | | | | | |
|---|---|---|---|---|---|---|---|---|---|---|---|
| Donor | HLA-DRB1 Typing | 267-281 | 280-299 | 299-317 | 320-337 | 342-356 | 363-380 | 374-388 | 410-424 | 416-433 | Total |
| 877 | 01:01/13:01 | 2 | 2 | | | | 1 | 1 | | | 13 |
| 829 | 07:01/15:01 | | 2 | | | | | 2 | 1 | | 9 |
| 876 | 11:01/11:04 | | 1 | 4 | | | 2 | 2 | | 3 | 18 |
| 996 | 08:04/14:08 | | 4 | 1 | | | | 1 | | 2 | 20 |
| 14 | 07:01/13:01 | | 2 | 1 | 1 | 1 | 2 | 7 | | 13 | 35 |
| 22 | 01:01/09:01 | | 3 | 8 | | | | 2 | 3 | 2 | 31 |
| 23 | 04:01/13:01 | 2 | 1 | 1 | | | 1 | 2 | 1 | 5 | 20 |
| 26 | 11:04/15:01 | | 3 | 1 | | | | | | 1 | 15 |
| 30 | 07:01/11:01 | | 1 | 3 | 1 | 1 | 1 | 3 | 1 | 2 | 20 |
| 32 | 03:01 | 3 | 1 | 2 | 1 | 1 | | | | 1 | 10 |
| 62 | 01:01/04:05 | 1 | | | | | | | 1 | | 13 |
| 31 | 13:01/16:01 | 1 | 3 | 6 | 2 | | | 1 | | 5 | 33 |
| 56 | 07:01/11:01 | 1 | | 6 | 1 | 2 | | 7 | 1 | 5 | 37 |
| | total | 10 | 23 | 33 | 6 | 5 | 7 | 28 | 8 | 39 | 274 |
| | Average strength (%) | 1.5 | 3.5 | 5.0 | 1.0 | 0.8 | 1.1 | 4.3 | 1.2 | 6.1 | |
| | responders | 6 | 11 | 10 | 5 | 4 | 5 | 10 | 6 | 10 | |
| | frequency | 46% | 85% | 77% | 38% | 31% | 38% | 77% | 46% | 77% | |

The peptides which are immunodominant in vitro are indicated in bold.
The most immunogenic peptides (highest frequency of responders and highest number of lines) are shaded.

EXAMPLE 6: RECOGNITION OF CCNB1 BY THE CD4+ T LYMPHOCYTES

In order to evaluate the capacity of the CD4+ T lymphocytes to recognize the CCNB1 protein, a part of the CD4+ T lymphocyte lines was cultured in the presence of autologous dendritic cells preloaded with CCNB1 and then the activation thereof was tested by IFN-gamma Elispot. Examples of responses to the CCNB1 protein are presented in FIG. 2A. All of the peptides which generated CD4+ T lymphocytes capable of recognizing the CCNB1 protein are presented in FIG. 2B. Not all the peptides could be tested.

TABLE X

Amino acid sequences

| Name | Sequence | SEQ ID No. |
|---|---|---|
| CCNB1 | MALRVTRNSKINAENKAKINMAGAKRVPTAPAATSKPGLRPRTAL GDIGNKVSEQLQAKMPMKKEAKPSATGKVIDKKLPKPLEKVPMLV PVPVSEPVPEPEPEPEPEPVKEEKLSPEPILVDTASPSPMETSGC APAEEDLCQAFSDVILAVNDVDAEDGADPNLCSEYVKDIYAYLRQ LEEEQAVRPKYLLGREVTGNMRAILIDWLVQVQMKFRLLQETMYM TVSIIDRFMQNNCVPKKMLQLVGVTAMFIASKYEEMYPPEIGDFA FVTDNTYTKHQIRQMEMKILRALNFGLGRPLPLHFLRRASKIGEV DVEQHTLAKYLMELTMLDYDMVHFPPSQIAAGAFCLALKILDNGE WTPTLQHYLSYTEESLLPVMQHLAKNVVMVNQGLTKHMTVKNKYA TSKHAKISTLPQLNSALVQDLAKAVAKV | 1 |
| HA 306-318 | PKYVKQNTLKLAT | 2 |
| YKL | AAYAAAKAAALAA | 3 |
| A3 152-166 | EAEQLRAYLDGTGVE | 4 |

TABLE X-continued

Amino acid sequences

| Name | Sequence | SEQ ID No. |
|---|---|---|
| MT 2-16 | AKTIAYDEEARRGLE | 5 |
| B1 21-36 | TERVRLVTRHIYNREE | 6 |
| LOL 191-210 | ESWGAVWRIDTPDKLTGPFT | 7 |
| E2/E168 | AGDLLAIETDKATI | 8 |
| Oxy 271-287 | EKKYFAATQFEPLAARL | 9 |
| CCNB1 1-15 | MALRVTRNSKINAEN | 10 |
| CCNB1 9-23 | SKINAENKAKINMAG | 11 |
| CCNB1 17-31 | AKINMAGAKRVPTAP | 12 |
| CCNB1 25-39 | KRVPTAPAATSKPGL | 13 |
| CCNB1 37-51 | PGLRPRTALGDIGNK | 14 |
| CCNB1 43-57 | TALGDIGNKVSEQLQ | 15 |
| CCNB1 50-64 | NKVSEQLQAKMPMKK | 16 |
| CCNB1 54-68 | EQLQAKMPMKKEAKP | 17 |
| CCNB1 58-72 | AKMPMKKEAKPSATG | 18 |
| CCNB1 71-85 | TGKVIDKKLPKPLEK | 19 |
| CCNB1 77-91 | KKLPKPLEKVPMLVP | 20 |
| CCNB1 81-95 | KPLEKVPMLVPVPVS | 21 |
| CCNB1 87-101 | PMLVPVPVSEPVPEP | 22 |
| CCNB1 96-110 | EPVPEPEPEPEPEPV | 23 |
| CCNB1 108-122 | EPVKEEKLSPEPILV | 24 |
| CCNB1 113-127 | EKLSPEPILVDTASP | 25 |
| CCNB1 118-132 | EPILVDTASPSPMET | 26 |
| CCNB1 128-142 | SPMETSGCAPAEEDL | 27 |
| CCNB1 140-154 | EDLCQAFSDVILAVN | 28 |
| CCNB1 144-158 | QAFSDVILAVNDVDA | 29 |
| CCNB1 147-161 | SDVILAVNDVDAEDG | 30 |
| CCNB1 151-165 | LAVNDVDAEDGADPN | 31 |
| CCNB1 164-178 | PNLCSEYVKDIYAYL | 32 |
| CCNB1 168-182 | SEYVKDIYAYLRQLE | 33 |
| CCNB1 172-186 | KDIYAYLRQLEEEQA | 34 |
| CCNB1 179-193 | RQLEEEQAVRPKYLL | 35 |
| CCNB1 185-199 | QAVRPKYLLGREVTG | 36 |
| CCNB1 189-203 | PKYLLGREVTGNMRA | 37 |
| CCNB1 195-209 | REVTGNMRAILIDWL | 38 |
| CCNB1 199-213 | GNMRAILIDWLVQVQ | 39 |
| CCNB1 202-216 | RAILIDWLVQVQMKF | 40 |
| CCNB1 207-221 | DWLVQVQMKFRLLQE | 41 |

TABLE X-continued

Amino acid sequences

| Name | Sequence | SEQ ID No. |
|---|---|---|
| CCNB1 212-226 | VQMKFRLLQETMYMT | 42 |
| CCNB1 216-230 | FRLLQETMYMTVSII | 43 |
| CCNB1 221-235 | ETMYMTVSIIDRFMQ | 44 |
| CCNB1 225-239 | MTVSIIDRFMQNNCV | 45 |
| CCNB1 231-245 | DRFMQNNCVPKKMLQ | 46 |
| CCNB1 237-251 | NCVPKKMLQLVGVTA | 47 |
| CCNB1 241-255 | KKMLQLVGVTAMFIA | 48 |
| CCNB1 244-258 | LQLVGVTAMFIASKY | 49 |
| CCNB1 250-264 | TAMFIASKYEEMYPP | 50 |
| CCNB1 256-270 | SKYEEMYPPEIGDFA | 51 |
| CCNB1 260-274 | EMYPPEIGDFAFVTD | 52 |
| CCNB1 264-278 | PEIGDFAFVTDNTYT | 53 |
| CCNB1 267-281 | GDFAFVTDNTYTKHQ | 54 |
| CCNB1 269-283 | FAFVTDNTYTKHQIR | 55 |
| CCNB1 275-289 | NTYTKHQIRQMEMKI | 56 |
| CCNB1 280-294 | HQIRQMEMKILRALN | 57 |
| CCNB1 285-299 | MEMKILRALNFGLGR | 58 |
| CCNB1 291-305 | RALNFGLGRPLPLHF | 59 |
| CCNB1 299-313 | RPLPLHFLRRASKIG | 60 |
| CCNB1 303-317 | LHFLRRASKIGEVDV | 61 |
| CCNB1 310-324 | SKIGEVDVEQHTLAK | 62 |
| CCNB1 315-329 | VDVEQHTLAKYLMEL | 63 |
| CCNB1 320-334 | HTLAKYLMELTMLDY | 64 |
| CCNB1 323-337 | AKYLMELTMLDYDMV | 65 |
| CCNB1 327-341 | MELTMLDYDMVHFPP | 66 |
| CCNB1 332-346 | LDYDMVHFPPSQIAA | 67 |
| CCNB1 338-352 | HFPPSQIAAGAFCLA | 68 |
| CCNB1 342-356 | SQIAAGAFCLALKIL | 69 |
| CCNB1 347-361 | GAFCLALKILDNGEW | 70 |
| CCNB1 351-365 | LALKILDNGEWTPTL | 71 |
| CCNB1 359-373 | GEWTPTLQHYLSYTE | 72 |
| CCNB1 363-377 | PTLQHYLSYTEESLL | 73 |
| CCNB1 366-380 | QHYLSYTEESLLPVM | 74 |
| CCNB1 369-383 | LSYTEESLLPVMQHL | 75 |
| CCNB1 374-388 | ESLLPVMQHLAKNVV | 76 |
| CCNB1 377-391 | LPVMQHLAKNVVMVN | 77 |
| CCNB1 385-399 | KNVVMVNQGLTKHMT | 78 |

TABLE X-continued

Amino acid sequences

| Name | Sequence | SEQ ID No. |
|---|---|---|
| CCNB1 392-406 | QGLTKHMTVKNKYAT | 79 |
| CCNB1 396-410 | KHMTVKNKYATSKHA | 80 |
| CCNB1 402-416 | NKYATSKHAKISTLP | 81 |
| CCNB1 410-424 | AKISTLPQLNSALVQ | 82 |
| CCNB1 416-430 | PQLNSALVQDLAKAV | 83 |
| CCNB1 419-433 | NSALVQDLAKAVAKV | 84 |
| CCNB1 199-216 | GNMRAILIDWLVQVQMKF | 85 |
| CCNB1 241-258 | KKMLQLVGVTAMFIASKY | 86 |
| CCNB1 280-299 | HQIRQMEMKILRALNFGLGR | 87 |
| CCNB1 299-317 | RPLPLHFLRRASKIGEVDV | 88 |
| CCNB1 320-337 | HTLAKYLMELTMLDYDMV | 89 |
| CCNB1 363-380 | PTLQHYLSYTEESLLPVM | 90 |
| CCNB1 416-433 | PQLNSALVQDLAKAVAKV | 91 |
| survivin 96-104 | LTLGEFLKL | 92 |
| survivin 95-104 | ELTLGEFLKL | 93 |
| survivin-2B 80-88 | AYACNTSTL | 94 |
| PADRE | KXVAAWTLKAA | 95 |
| P1 | AGYLMELCV | 96 |
| P2 | AGYLMELCM | 97 |
| P3 | AGYLMELCF | 98 |
| P4 | AGYLMELCC | 99 |
| P5 | AGYLMELCMA | 100 |
| P6 | AGYLMELCFA | 101 |
| CB9 | AKYLMELTM | 102 |
| CB10 | AKYLMELTML | 103 |
| CB9L2 | ALYLMELTM | 104 |
| CB9M2 | AMYLMELTM | 105 |
| CB204 | ILIDWLVQV | 106 |
| CB215-229 | KFRLLQETMYMTVSI | 107 |
| CB219-233 | LQETMYMTVSIIDRF | 108 |
| CB223-234 | MYMTVSIIDRFM | 109 |

The invention claimed is:

1. A method of inducing a cyclin B1-specific human CD4+ T lymphocyte response in a subject, the method comprising administering a peptide to the subject, the said peptide consisting of a sequence of from 11 to 30 amino acids which is derived from the human cyclin B1 sequence of SEQ ID NO: 1 and which comprises at least one human cyclin B1 CD4+ T epitope which is immunodominant in vitro, said peptide being selected from the group consisting of:
   a) the sequences of 11 to 30 consecutive amino acids of the human cyclin B1 sequence of SEQ ID NO: 1 comprising at least residues 3 to 11, 19 to 27, 376 to 384, 27 to 35, 120 to 128, 282 to 290, 287 to 295, 305 to 313, 317 to 325, 322 to 330, 325 to 333, 379 to 387, 412 to 420, 418 to 426 or 422 to 430 of said sequence SEQ ID NO: 1, and
   b) the sequences of 11 to 30 amino acids having at least 70% identity with a sequence in a), with the exclusion of the sequence of 15 amino acids made up of residues 279 to 293 of said sequence SEQ ID NO: 1,
said peptide being capable of stimulating a cyclin B1-specific human CD4+ T lymphocyte response.

2. The method as claimed in claim 1, characterized in that the average strength of the in vitro response of human CD4+ T lymphocytes specific for said peptide is at least 2.5% in a group of subjects expressing varied HLA II molecules including at least the HLA-DR1, HLA-DR3, HLA-DR4, HLA-DR7, HLA-DR11, HLA-DR13 and HLA-DR15 molecules, and the frequency of responders in vitro to said peptide is at least 55% in said group of subjects.

3. The method as claimed in claim 1, characterized in that the said peptide is selected from the group consisting of the sequences SEQ ID NO: 10, 12, 13, 26, 57, 58, 61, 63, 64, 65, 76, 77, 82, 83, 84, 87, 88, 89 and 91.

4. The method as claimed in claim 1, characterized in that the said peptide is a mixture of peptides comprising: (i) at least one first peptide comprising a cyclin B1 CD4+ T epitope which is immunodominant in vitro, as defined in claim 1, and (ii) at least one second peptide comprising at least one CD4+ T epitope other than said epitope which is immunodominant in vitro, and/or one CD8+ T epitope, and/or one B epitope.

5. The method as claimed in claim 4, characterized in that the said second peptide is a peptide comprising a cyclin B1 CD4+ T epitope, capable of binding to at least 6 different predominant HLA II molecules chosen from the HLA-DR1, HLA-DR3, HLA-DR4, HLA-DR7, HLA-DR11, HLA-DR13, HLA-DR15, HLA-DRB3, HLA-DRB4, HLA-DRB5, HLA-DP401 and HLA-DP402 molecules, selected from the group made up of: a) the sequences of 11 to 30 consecutive amino acids of the human cyclin B1 sequence of SEQ ID NO: 1 comprising at least residues 170-178, 201-209, 204-212, 209-217, 214-222, 218-226, 223-231, 227-235, 243-251, 246-254, 252-260, 269-277, 301-309, 344-352, 365-373, 368-376 or 371-379 of said sequence SEQ ID NO: 1, and b) the sequences of 11 to 30 amino acids having at least 70% identity with a sequence in a).

6. The method as claimed in claim 5, characterized in that the said second peptide is selected from the group consisting of the sequences SEQ ID NO: 33, 39, 40, 41, 42, 43, 44, 45, 48, 49, 50, 54, 60, 69, 73, 74, 75, 85, 86 and 90.

7. The method as claimed in claim 4, characterized in that the said second peptide is a peptide comprising a cyclin B1 CD4+ T epitope, capable of binding to 3 to 5 different predominant HLA II molecules chosen from the HLA-DR1, HLA-DR3, HLA-DR4, HLA-DR7, HLA-DR11, HLA-DR13, HLA-DR15, HLA-DRB3, HLA-DRB4, HLA-DRB5, HLA-DP401 and HLA-DP402 molecules, selected from the group consisting of: a) the sequences of 11 to 30 consecutive amino acids of the human cyclin B1 sequence of SEQ ID NO: 1 comprising at least residues 115-123, 146-154, 166-174, 172-180,187-195, 191-199, 197-205, 239-247, 266-274, 271-279, 277-285, 293-301, 329-337, 361-369 or 387-395 of said sequence SEQ ID NO: 1, and b) the sequences of 11 to 30 amino acids having at least 70% identity with a sequence in a).

8. The method as claimed in claim 7, characterized in that the said second peptide is selected from the group consisting of the sequences SEQ ID NO: 25, 29, 32, 34, 36, 37, 38, 47, 53, 55, 56, 59, 66, 72 and 78.

9. The method as claimed in claim 4, characterized in that the said peptides are linked to one another in the form of a multi-epitope polypeptide.

10. The method as claimed in claim 1, characterized in that the said peptide is a modified peptide derived from the peptide as claimed in claim 1 through the introduction of a chemical modification, said modified peptide comprising at least one human cyclin B1 CD4+ T epitope which is immunodominant in vitro and being capable of stimulating a cyclin β1-specific human CD4+ T lymphocyte response.

11. The method as claimed in claim 9, characterized in that the said multi-epitope polypeptide is a modified polypeptide derived from the multi-epitope polypeptide as claimed in claim 9 through the introduction of a chemical modification, said modified polypeptide comprising at least one human cyclin B1 CD4$^+$ T epitope which is immunodominant in vitro and being capable of stimulating a cyclin B1-specific human CD4$^+$ T lymphocyte, response.

12. The method as claimed in claim 1, characterized in that the said peptide is comprised within an immunogenic or vaccine composition.

13. The method as claimed in claim 1, characterized in that the said subject has a cancer.

14. The method as claimed in claim 13, characterized in that the said cancer is selected from the group consisting of breast, colon, prostate, esophagus, stomach, lung, head and neck cancers.

15. A method of immunotherapy in a subject having a cancer associated with the overexpression of cyclin B1, comprising the induction of a cyclin B1-specific human CD4$^+$ T lymphocyte response in the subject according to the method of claim 1.

16. The method as claimed in claim 15, characterized in that the said cancer is selected from the group consisting of breast, colon, prostate, esophagus, stomach, lung, head and neck cancers.

* * * * *

SEQUENCE LISTING

<160> NUMBER OF SEQ ID NOS: 109

<210> SEQ ID NO 1
<211> LENGTH: 433
<212> TYPE: PRT
<213> ORGANISM: Homo sapiens

<400> SEQUENCE: 1

Met Ala Leu Arg Val Thr Arg Asn Ser Lys Ile Asn Ala Glu Asn Lys
1               5                   10                  15

Ala Lys Ile Asn Met Ala Gly Ala Lys Arg Val Pro Thr Ala Pro Ala
            20                  25                  30

Ala Thr Ser Lys Pro Gly Leu Arg Pro Arg Thr Ala Leu Gly Asp Ile
        35                  40                  45

Gly Asn Lys Val Ser Glu Gln Leu Gln Ala Lys Met Pro Met Lys Lys
    50                  55                  60

Glu Ala Lys Pro Ser Ala Thr Gly Lys Val Ile Asp Lys Lys Leu Pro
65                  70                  75                  80

Lys Pro Leu Glu Lys Val Pro Met Leu Val Pro Val Pro Val Ser Glu
                85                  90                  95

Pro Val Pro Glu Pro Glu Pro Glu Pro Glu Pro Val Lys Glu
            100                 105                 110

Glu Lys Leu Ser Pro Glu Pro Ile Leu Val Asp Thr Ala Ser Pro Ser
            115                 120                 125

Pro Met Glu Thr Ser Gly Cys Ala Pro Ala Glu Glu Asp Leu Cys Gln
    130                 135                 140

Ala Phe Ser Asp Val Ile Leu Ala Val Asn Asp Val Asp Ala Glu Asp
145                 150                 155                 160

Gly Ala Asp Pro Asn Leu Cys Ser Glu Tyr Val Lys Asp Ile Tyr Ala
                165                 170                 175

Tyr Leu Arg Gln Leu Glu Glu Glu Gln Ala Val Arg Pro Lys Tyr Leu
            180                 185                 190

Leu Gly Arg Glu Val Thr Gly Asn Met Arg Ala Ile Leu Ile Asp Trp
        195                 200                 205

Leu Val Gln Val Gln Met Lys Phe Arg Leu Leu Gln Glu Thr Met Tyr
    210                 215                 220

Met Thr Val Ser Ile Ile Asp Arg Phe Met Gln Asn Asn Cys Val Pro
225                 230                 235                 240

Lys Lys Met Leu Gln Leu Val Gly Val Thr Ala Met Phe Ile Ala Ser
                245                 250                 255

Lys Tyr Glu Glu Met Tyr Pro Pro Glu Ile Gly Asp Phe Ala Phe Val
            260                 265                 270

Thr Asp Asn Thr Tyr Thr Lys His Gln Ile Arg Gln Met Glu Met Lys
        275                 280                 285

Ile Leu Arg Ala Leu Asn Phe Gly Leu Gly Arg Pro Leu Pro Leu His
    290                 295                 300

Phe Leu Arg Arg Ala Ser Lys Ile Gly Glu Val Asp Val Glu Gln His
305                 310                 315                 320

Thr Leu Ala Lys Tyr Leu Met Glu Leu Thr Met Leu Asp Tyr Asp Met
                325                 330                 335

Val His Phe Pro Pro Ser Gln Ile Ala Ala Gly Ala Phe Cys Leu Ala
            340                 345                 350

Leu Lys Ile Leu Asp Asn Gly Glu Trp Thr Pro Thr Leu Gln His Tyr
        355                 360                 365

```
Leu Ser Tyr Thr Glu Glu Ser Leu Leu Pro Val Met Gln His Leu Ala
        370                 375                 380

Lys Asn Val Val Met Val Asn Gln Gly Leu Thr Lys His Met Thr Val
385                 390                 395                 400

Lys Asn Lys Tyr Ala Thr Ser Lys His Ala Lys Ile Ser Thr Leu Pro
                405                 410                 415

Gln Leu Asn Ser Ala Leu Val Gln Asp Leu Ala Lys Ala Val Ala Lys
                420                 425                 430

Val

<210> SEQ ID NO 2
<211> LENGTH: 13
<212> TYPE: PRT
<213> ORGANISM: Artificial sequence
<220> FEATURE:
<223> OTHER INFORMATION: synthetic peptide HA 306-318

<400> SEQUENCE: 2

Pro Lys Tyr Val Lys Gln Asn Thr Leu Lys Leu Ala Thr
1               5                   10

<210> SEQ ID NO 3
<211> LENGTH: 13
<212> TYPE: PRT
<213> ORGANISM: Artificial sequence
<220> FEATURE:
<223> OTHER INFORMATION: synthetic peptide YKL

<400> SEQUENCE: 3

Ala Ala Tyr Ala Ala Ala Lys Ala Ala Ala Leu Ala Ala
1               5                   10

<210> SEQ ID NO 4
<211> LENGTH: 15
<212> TYPE: PRT
<213> ORGANISM: Artificial sequence
<220> FEATURE:
<223> OTHER INFORMATION: synthetic peptide A3 152-166

<400> SEQUENCE: 4

Glu Ala Glu Gln Leu Arg Ala Tyr Leu Asp Gly Thr Gly Val Glu
1               5                   10                  15

<210> SEQ ID NO 5
<211> LENGTH: 15
<212> TYPE: PRT
<213> ORGANISM: Artificial sequence
<220> FEATURE:
<223> OTHER INFORMATION: synthetic peptide MT 2-16

<400> SEQUENCE: 5

Ala Lys Thr Ile Ala Tyr Asp Glu Glu Ala Arg Arg Gly Leu Glu
1               5                   10                  15

<210> SEQ ID NO 6
<211> LENGTH: 16
<212> TYPE: PRT
<213> ORGANISM: Artificial sequence
<220> FEATURE:
<223> OTHER INFORMATION: synthetic peptide B1 21-36

<400> SEQUENCE: 6

Thr Glu Arg Val Arg Leu Val Thr Arg His Ile Tyr Asn Arg Glu Glu
1               5                   10                  15
```

<210> SEQ ID NO 7
<211> LENGTH: 20
<212> TYPE: PRT
<213> ORGANISM: Artificial sequence
<220> FEATURE:
<223> OTHER INFORMATION: synthetic peptide LOL 191-210

<400> SEQUENCE: 7

```
Glu Ser Trp Gly Ala Val Trp Arg Ile Asp Thr Pro Asp Lys Leu Thr
1               5                   10                  15

Gly Pro Phe Thr
            20
```

<210> SEQ ID NO 8
<211> LENGTH: 14
<212> TYPE: PRT
<213> ORGANISM: Artificial sequence
<220> FEATURE:
<223> OTHER INFORMATION: synthetic peptide E2/E168

<400> SEQUENCE: 8

```
Ala Gly Asp Leu Leu Ala Ile Glu Thr Asp Lys Ala Thr Ile
1               5                   10
```

<210> SEQ ID NO 9
<211> LENGTH: 17
<212> TYPE: PRT
<213> ORGANISM: Artificial sequence
<220> FEATURE:
<223> OTHER INFORMATION: synthetic peptide Oxy 271-287

<400> SEQUENCE: 9

```
Glu Lys Lys Tyr Phe Ala Ala Thr Gln Phe Glu Pro Leu Ala Ala Arg
1               5                   10                  15

Leu
```

<210> SEQ ID NO 10
<211> LENGTH: 15
<212> TYPE: PRT
<213> ORGANISM: Artificial sequence
<220> FEATURE:
<223> OTHER INFORMATION: synthetic peptide CCNB1 1-15

<400> SEQUENCE: 10

```
Met Ala Leu Arg Val Thr Arg Asn Ser Lys Ile Asn Ala Glu Asn
1               5                   10                  15
```

<210> SEQ ID NO 11
<211> LENGTH: 15
<212> TYPE: PRT
<213> ORGANISM: Artificial sequence
<220> FEATURE:
<223> OTHER INFORMATION: synthetic peptide CCNB1 9-23

<400> SEQUENCE: 11

```
Ser Lys Ile Asn Ala Glu Asn Lys Ala Lys Ile Asn Met Ala Gly
1               5                   10                  15
```

<210> SEQ ID NO 12
<211> LENGTH: 15
<212> TYPE: PRT
<213> ORGANISM: Artificial sequence
<220> FEATURE:
<223> OTHER INFORMATION: synthetic peptide CCNB1 17-31

<400> SEQUENCE: 12

```
Ala Lys Ile Asn Met Ala Gly Ala Lys Arg Val Pro Thr Ala Pro
1               5                   10                  15

<210> SEQ ID NO 13
<211> LENGTH: 15
<212> TYPE: PRT
<213> ORGANISM: Artificial sequence
<220> FEATURE:
<223> OTHER INFORMATION: synthetic peptide CCNB1 25-39

<400> SEQUENCE: 13

Lys Arg Val Pro Thr Ala Pro Ala Ala Thr Ser Lys Pro Gly Leu
1               5                   10                  15

<210> SEQ ID NO 14
<211> LENGTH: 15
<212> TYPE: PRT
<213> ORGANISM: Artificial sequence
<220> FEATURE:
<223> OTHER INFORMATION: synthetic peptide CCNB1 37-51

<400> SEQUENCE: 14

Pro Gly Leu Arg Pro Arg Thr Ala Leu Gly Asp Ile Gly Asn Lys
1               5                   10                  15

<210> SEQ ID NO 15
<211> LENGTH: 15
<212> TYPE: PRT
<213> ORGANISM: Artificial sequence
<220> FEATURE:
<223> OTHER INFORMATION: synthetic peptide CCNB1 43-57

<400> SEQUENCE: 15

Thr Ala Leu Gly Asp Ile Gly Asn Lys Val Ser Glu Gln Leu Gln
1               5                   10                  15

<210> SEQ ID NO 16
<211> LENGTH: 15
<212> TYPE: PRT
<213> ORGANISM: Artificial sequence
<220> FEATURE:
<223> OTHER INFORMATION: synthetic peptide CCNB1 50-64

<400> SEQUENCE: 16

Asn Lys Val Ser Glu Gln Leu Gln Ala Lys Met Pro Met Lys Lys
1               5                   10                  15

<210> SEQ ID NO 17
<211> LENGTH: 15
<212> TYPE: PRT
<213> ORGANISM: Artificial sequence
<220> FEATURE:
<223> OTHER INFORMATION: synthetic peptide CCNB1 54-68

<400> SEQUENCE: 17

Glu Gln Leu Gln Ala Lys Met Pro Met Lys Lys Glu Ala Lys Pro
1               5                   10                  15

<210> SEQ ID NO 18
<211> LENGTH: 15
<212> TYPE: PRT
<213> ORGANISM: Artificial sequence
<220> FEATURE:
<223> OTHER INFORMATION: synthetic peptide CCNB1 58-72

<400> SEQUENCE: 18
```

```
Ala Lys Met Pro Met Lys Lys Glu Ala Lys Pro Ser Ala Thr Gly
1               5                   10                  15

<210> SEQ ID NO 19
<211> LENGTH: 15
<212> TYPE: PRT
<213> ORGANISM: Artificial sequence
<220> FEATURE:
<223> OTHER INFORMATION: synthetic peptide CCNB1 71-85

<400> SEQUENCE: 19

Thr Gly Lys Val Ile Asp Lys Lys Leu Pro Lys Pro Leu Glu Lys
1               5                   10                  15

<210> SEQ ID NO 20
<211> LENGTH: 15
<212> TYPE: PRT
<213> ORGANISM: Artificial sequence
<220> FEATURE:
<223> OTHER INFORMATION: synthetic peptide CCNB1 77-91

<400> SEQUENCE: 20

Lys Lys Leu Pro Lys Pro Leu Glu Lys Val Pro Met Leu Val Pro
1               5                   10                  15

<210> SEQ ID NO 21
<211> LENGTH: 15
<212> TYPE: PRT
<213> ORGANISM: Artificial sequence
<220> FEATURE:
<223> OTHER INFORMATION: synthetic peptide CCNB1 81-95

<400> SEQUENCE: 21

Lys Pro Leu Glu Lys Val Pro Met Leu Val Pro Val Pro Val Ser
1               5                   10                  15

<210> SEQ ID NO 22
<211> LENGTH: 15
<212> TYPE: PRT
<213> ORGANISM: Artificial sequence
<220> FEATURE:
<223> OTHER INFORMATION: synthetic peptide CCNB1 87-101

<400> SEQUENCE: 22

Pro Met Leu Val Pro Val Pro Val Ser Glu Pro Val Pro Glu Pro
1               5                   10                  15

<210> SEQ ID NO 23
<211> LENGTH: 15
<212> TYPE: PRT
<213> ORGANISM: Artificial sequence
<220> FEATURE:
<223> OTHER INFORMATION: synthetic peptide CCNB1 96-110

<400> SEQUENCE: 23

Glu Pro Val Pro Glu Pro Glu Pro Glu Pro Glu Pro Glu Pro Val
1               5                   10                  15

<210> SEQ ID NO 24
<211> LENGTH: 15
<212> TYPE: PRT
<213> ORGANISM: Artificial sequence
<220> FEATURE:
<223> OTHER INFORMATION: synthetic peptide CCNB1 108-122

<400> SEQUENCE: 24

Glu Pro Val Lys Glu Glu Lys Leu Ser Pro Glu Pro Ile Leu Val
```

```
<210> SEQ ID NO 25
<211> LENGTH: 15
<212> TYPE: PRT
<213> ORGANISM: Artificial sequence
<220> FEATURE:
<223> OTHER INFORMATION: synthetic peptide CCNB1 113-127

<400> SEQUENCE: 25

Glu Lys Leu Ser Pro Glu Pro Ile Leu Val Asp Thr Ala Ser Pro
1               5                   10                  15

<210> SEQ ID NO 26
<211> LENGTH: 15
<212> TYPE: PRT
<213> ORGANISM: Artificial sequence
<220> FEATURE:
<223> OTHER INFORMATION: synthetic peptide CCNB1 118-132

<400> SEQUENCE: 26

Glu Pro Ile Leu Val Asp Thr Ala Ser Pro Ser Pro Met Glu Thr
1               5                   10                  15

<210> SEQ ID NO 27
<211> LENGTH: 15
<212> TYPE: PRT
<213> ORGANISM: Artificial sequence
<220> FEATURE:
<223> OTHER INFORMATION: synthetic peptide CCNB1 128-142

<400> SEQUENCE: 27

Ser Pro Met Glu Thr Ser Gly Cys Ala Pro Ala Glu Glu Asp Leu
1               5                   10                  15

<210> SEQ ID NO 28
<211> LENGTH: 15
<212> TYPE: PRT
<213> ORGANISM: Artificial sequence
<220> FEATURE:
<223> OTHER INFORMATION: synthetic peptide CCNB1 140-154

<400> SEQUENCE: 28

Glu Asp Leu Cys Gln Ala Phe Ser Asp Val Ile Leu Ala Val Asn
1               5                   10                  15

<210> SEQ ID NO 29
<211> LENGTH: 15
<212> TYPE: PRT
<213> ORGANISM: Artificial sequence
<220> FEATURE:
<223> OTHER INFORMATION: synthetic peptide CCNB1 144-158

<400> SEQUENCE: 29

Gln Ala Phe Ser Asp Val Ile Leu Ala Val Asn Asp Val Asp Ala
1               5                   10                  15

<210> SEQ ID NO 30
<211> LENGTH: 15
<212> TYPE: PRT
<213> ORGANISM: Artificial sequence
<220> FEATURE:
<223> OTHER INFORMATION: synthetic peptide CCNB1 147-161

<400> SEQUENCE: 30

Ser Asp Val Ile Leu Ala Val Asn Asp Val Asp Ala Glu Asp Gly
1               5                   10                  15
```

<210> SEQ ID NO 31
<211> LENGTH: 15
<212> TYPE: PRT
<213> ORGANISM: Artificial sequence
<220> FEATURE:
<223> OTHER INFORMATION: synthetic peptide CCNB1 151-165

<400> SEQUENCE: 31

Leu Ala Val Asn Asp Val Asp Ala Glu Asp Gly Ala Asp Pro Asn
1               5                   10                  15

<210> SEQ ID NO 32
<211> LENGTH: 15
<212> TYPE: PRT
<213> ORGANISM: Artificial sequence
<220> FEATURE:
<223> OTHER INFORMATION: synthetic peptide CCNB1 164-178

<400> SEQUENCE: 32

Pro Asn Leu Cys Ser Glu Tyr Val Lys Asp Ile Tyr Ala Tyr Leu
1               5                   10                  15

<210> SEQ ID NO 33
<211> LENGTH: 15
<212> TYPE: PRT
<213> ORGANISM: Artificial sequence
<220> FEATURE:
<223> OTHER INFORMATION: synthetic peptide CCNB1 168-182

<400> SEQUENCE: 33

Ser Glu Tyr Val Lys Asp Ile Tyr Ala Tyr Leu Arg Gln Leu Glu
1               5                   10                  15

<210> SEQ ID NO 34
<211> LENGTH: 15
<212> TYPE: PRT
<213> ORGANISM: Artificial sequence
<220> FEATURE:
<223> OTHER INFORMATION: synthetic peptide CCNB1 172-186

<400> SEQUENCE: 34

Lys Asp Ile Tyr Ala Tyr Leu Arg Gln Leu Glu Glu Glu Gln Ala
1               5                   10                  15

<210> SEQ ID NO 35
<211> LENGTH: 15
<212> TYPE: PRT
<213> ORGANISM: Artificial sequence
<220> FEATURE:
<223> OTHER INFORMATION: synthetic peptide CCNB1 179-193

<400> SEQUENCE: 35

Arg Gln Leu Glu Glu Glu Gln Ala Val Arg Pro Lys Tyr Leu Leu
1               5                   10                  15

<210> SEQ ID NO 36
<211> LENGTH: 15
<212> TYPE: PRT
<213> ORGANISM: Artificial sequence
<220> FEATURE:
<223> OTHER INFORMATION: synthetic peptide CCNB1 185-199

<400> SEQUENCE: 36

Gln Ala Val Arg Pro Lys Tyr Leu Leu Gly Arg Glu Val Thr Gly
1               5                   10                  15

```
<210> SEQ ID NO 37
<211> LENGTH: 15
<212> TYPE: PRT
<213> ORGANISM: Artificial sequence
<220> FEATURE:
<223> OTHER INFORMATION: synthetic peptide CCNB1 189-203

<400> SEQUENCE: 37

Pro Lys Tyr Leu Leu Gly Arg Glu Val Thr Gly Asn Met Arg Ala
1               5                   10                  15

<210> SEQ ID NO 38
<211> LENGTH: 15
<212> TYPE: PRT
<213> ORGANISM: Artificial sequence
<220> FEATURE:
<223> OTHER INFORMATION: synthetic peptide CCNB1 195-209

<400> SEQUENCE: 38

Arg Glu Val Thr Gly Asn Met Arg Ala Ile Leu Ile Asp Trp Leu
1               5                   10                  15

<210> SEQ ID NO 39
<211> LENGTH: 15
<212> TYPE: PRT
<213> ORGANISM: Artificial sequence
<220> FEATURE:
<223> OTHER INFORMATION: synthetic peptide CCNB1 199-213

<400> SEQUENCE: 39

Gly Asn Met Arg Ala Ile Leu Ile Asp Trp Leu Val Gln Val Gln
1               5                   10                  15

<210> SEQ ID NO 40
<211> LENGTH: 15
<212> TYPE: PRT
<213> ORGANISM: Artificial sequence
<220> FEATURE:
<223> OTHER INFORMATION: synthetic peptide CCNB1 202-216

<400> SEQUENCE: 40

Arg Ala Ile Leu Ile Asp Trp Leu Val Gln Val Gln Met Lys Phe
1               5                   10                  15

<210> SEQ ID NO 41
<211> LENGTH: 15
<212> TYPE: PRT
<213> ORGANISM: Artificial sequence
<220> FEATURE:
<223> OTHER INFORMATION: synthetic peptide CCNB1 207-221

<400> SEQUENCE: 41

Asp Trp Leu Val Gln Val Gln Met Lys Phe Arg Leu Leu Gln Glu
1               5                   10                  15

<210> SEQ ID NO 42
<211> LENGTH: 15
<212> TYPE: PRT
<213> ORGANISM: Artificial sequence
<220> FEATURE:
<223> OTHER INFORMATION: synthetic peptide CCNB1 212-226

<400> SEQUENCE: 42

Val Gln Met Lys Phe Arg Leu Leu Gln Glu Thr Met Tyr Met Thr
1               5                   10                  15
```

-continued

<210> SEQ ID NO 43
<211> LENGTH: 15
<212> TYPE: PRT
<213> ORGANISM: Artificial sequence
<220> FEATURE:
<223> OTHER INFORMATION: synthetic peptide CCNB1 216-230

<400> SEQUENCE: 43

Phe Arg Leu Leu Gln Glu Thr Met Tyr Met Thr Val Ser Ile Ile
1               5                   10                  15

<210> SEQ ID NO 44
<211> LENGTH: 15
<212> TYPE: PRT
<213> ORGANISM: Artificial sequence
<220> FEATURE:
<223> OTHER INFORMATION: synthetic peptide CCNB1 221-235

<400> SEQUENCE: 44

Glu Thr Met Tyr Met Thr Val Ser Ile Ile Asp Arg Phe Met Gln
1               5                   10                  15

<210> SEQ ID NO 45
<211> LENGTH: 15
<212> TYPE: PRT
<213> ORGANISM: Artificial sequence
<220> FEATURE:
<223> OTHER INFORMATION: synthetic peptide CCNB1 225-239

<400> SEQUENCE: 45

Met Thr Val Ser Ile Ile Asp Arg Phe Met Gln Asn Asn Cys Val
1               5                   10                  15

<210> SEQ ID NO 46
<211> LENGTH: 15
<212> TYPE: PRT
<213> ORGANISM: Artificial sequence
<220> FEATURE:
<223> OTHER INFORMATION: synthetic peptide CCNB1 231-245

<400> SEQUENCE: 46

Asp Arg Phe Met Gln Asn Asn Cys Val Pro Lys Lys Met Leu Gln
1               5                   10                  15

<210> SEQ ID NO 47
<211> LENGTH: 15
<212> TYPE: PRT
<213> ORGANISM: Artificial sequence
<220> FEATURE:
<223> OTHER INFORMATION: synthetic peptide CCNB1 237-251

<400> SEQUENCE: 47

Asn Cys Val Pro Lys Lys Met Leu Gln Leu Val Gly Val Thr Ala
1               5                   10                  15

<210> SEQ ID NO 48
<211> LENGTH: 15
<212> TYPE: PRT
<213> ORGANISM: Artificial sequence
<220> FEATURE:
<223> OTHER INFORMATION: synthetic peptide CCNB1 241-255

<400> SEQUENCE: 48

Lys Lys Met Leu Gln Leu Val Gly Val Thr Ala Met Phe Ile Ala
1               5                   10                  15

<210> SEQ ID NO 49

```
<211> LENGTH: 15
<212> TYPE: PRT
<213> ORGANISM: Artificial sequence
<220> FEATURE:
<223> OTHER INFORMATION: synthetic peptide CCNB1 244-258

<400> SEQUENCE: 49

Leu Gln Leu Val Gly Val Thr Ala Met Phe Ile Ala Ser Lys Tyr
1               5                   10                  15

<210> SEQ ID NO 50
<211> LENGTH: 15
<212> TYPE: PRT
<213> ORGANISM: Artificial sequence
<220> FEATURE:
<223> OTHER INFORMATION: synthetic peptide CCNB1 250-264

<400> SEQUENCE: 50

Thr Ala Met Phe Ile Ala Ser Lys Tyr Glu Glu Met Tyr Pro Pro
1               5                   10                  15

<210> SEQ ID NO 51
<211> LENGTH: 15
<212> TYPE: PRT
<213> ORGANISM: Artificial sequence
<220> FEATURE:
<223> OTHER INFORMATION: synthetic peptide CCNB1 256-270

<400> SEQUENCE: 51

Ser Lys Tyr Glu Glu Met Tyr Pro Pro Glu Ile Gly Asp Phe Ala
1               5                   10                  15

<210> SEQ ID NO 52
<211> LENGTH: 15
<212> TYPE: PRT
<213> ORGANISM: Artificial sequence
<220> FEATURE:
<223> OTHER INFORMATION: synthetic peptide CCNB1 260-274

<400> SEQUENCE: 52

Glu Met Tyr Pro Pro Glu Ile Gly Asp Phe Ala Phe Val Thr Asp
1               5                   10                  15

<210> SEQ ID NO 53
<211> LENGTH: 15
<212> TYPE: PRT
<213> ORGANISM: Artificial sequence
<220> FEATURE:
<223> OTHER INFORMATION: synthetic peptide CCNB1 264-278

<400> SEQUENCE: 53

Pro Glu Ile Gly Asp Phe Ala Phe Val Thr Asp Asn Thr Tyr Thr
1               5                   10                  15

<210> SEQ ID NO 54
<211> LENGTH: 15
<212> TYPE: PRT
<213> ORGANISM: Artificial sequence
<220> FEATURE:
<223> OTHER INFORMATION: synthetic peptide CCNB1 267-281

<400> SEQUENCE: 54

Gly Asp Phe Ala Phe Val Thr Asp Asn Thr Tyr Thr Lys His Gln
1               5                   10                  15

<210> SEQ ID NO 55
<211> LENGTH: 15
```

```
<212> TYPE: PRT
<213> ORGANISM: Artificial sequence
<220> FEATURE:
<223> OTHER INFORMATION: synthetic peptide CCNB1 269-283

<400> SEQUENCE: 55

Phe Ala Phe Val Thr Asp Asn Thr Tyr Thr Lys His Gln Ile Arg
1               5                   10                  15

<210> SEQ ID NO 56
<211> LENGTH: 15
<212> TYPE: PRT
<213> ORGANISM: Artificial sequence
<220> FEATURE:
<223> OTHER INFORMATION: synthetic peptide CCNB1 275-289

<400> SEQUENCE: 56

Asn Thr Tyr Thr Lys His Gln Ile Arg Gln Met Glu Met Lys Ile
1               5                   10                  15

<210> SEQ ID NO 57
<211> LENGTH: 15
<212> TYPE: PRT
<213> ORGANISM: Artificial sequence
<220> FEATURE:
<223> OTHER INFORMATION: synthetic peptide CCNB1 280-294

<400> SEQUENCE: 57

His Gln Ile Arg Gln Met Glu Met Lys Ile Leu Arg Ala Leu Asn
1               5                   10                  15

<210> SEQ ID NO 58
<211> LENGTH: 15
<212> TYPE: PRT
<213> ORGANISM: Artificial sequence
<220> FEATURE:
<223> OTHER INFORMATION: synthetic peptide CCNB1 285-299

<400> SEQUENCE: 58

Met Glu Met Lys Ile Leu Arg Ala Leu Asn Phe Gly Leu Gly Arg
1               5                   10                  15

<210> SEQ ID NO 59
<211> LENGTH: 15
<212> TYPE: PRT
<213> ORGANISM: Artificial sequence
<220> FEATURE:
<223> OTHER INFORMATION: synthetic peptide CCNB1 291-305

<400> SEQUENCE: 59

Arg Ala Leu Asn Phe Gly Leu Gly Arg Pro Leu Pro Leu His Phe
1               5                   10                  15

<210> SEQ ID NO 60
<211> LENGTH: 15
<212> TYPE: PRT
<213> ORGANISM: Artificial sequence
<220> FEATURE:
<223> OTHER INFORMATION: synthetic peptide CCNB1 299-313

<400> SEQUENCE: 60

Arg Pro Leu Pro Leu His Phe Leu Arg Arg Ala Ser Lys Ile Gly
1               5                   10                  15

<210> SEQ ID NO 61
<211> LENGTH: 15
<212> TYPE: PRT
```

-continued

<210> SEQ ID NO 61
<211> LENGTH: 15
<212> TYPE: PRT
<213> ORGANISM: Artificial sequence
<220> FEATURE:
<223> OTHER INFORMATION: synthetic peptide CCNB1 303-317

<400> SEQUENCE: 61

Leu His Phe Leu Arg Arg Ala Ser Lys Ile Gly Glu Val Asp Val
1               5                   10                  15

<210> SEQ ID NO 62
<211> LENGTH: 15
<212> TYPE: PRT
<213> ORGANISM: Artificial sequence
<220> FEATURE:
<223> OTHER INFORMATION: synthetic peptide CCNB1 310-324

<400> SEQUENCE: 62

Ser Lys Ile Gly Glu Val Asp Val Glu Gln His Thr Leu Ala Lys
1               5                   10                  15

<210> SEQ ID NO 63
<211> LENGTH: 15
<212> TYPE: PRT
<213> ORGANISM: Artificial sequence
<220> FEATURE:
<223> OTHER INFORMATION: synthetic peptide CCNB1 315-329

<400> SEQUENCE: 63

Val Asp Val Glu Gln His Thr Leu Ala Lys Tyr Leu Met Glu Leu
1               5                   10                  15

<210> SEQ ID NO 64
<211> LENGTH: 15
<212> TYPE: PRT
<213> ORGANISM: Artificial sequence
<220> FEATURE:
<223> OTHER INFORMATION: synthetic peptide CCNB1 320-334

<400> SEQUENCE: 64

His Thr Leu Ala Lys Tyr Leu Met Glu Leu Thr Met Leu Asp Tyr
1               5                   10                  15

<210> SEQ ID NO 65
<211> LENGTH: 15
<212> TYPE: PRT
<213> ORGANISM: Artificial sequence
<220> FEATURE:
<223> OTHER INFORMATION: synthetic peptide CCNB1 323-337

<400> SEQUENCE: 65

Ala Lys Tyr Leu Met Glu Leu Thr Met Leu Asp Tyr Asp Met Val
1               5                   10                  15

<210> SEQ ID NO 66
<211> LENGTH: 15
<212> TYPE: PRT
<213> ORGANISM: Artificial sequence
<220> FEATURE:
<223> OTHER INFORMATION: synthetic peptide CCNB1 327-341

<400> SEQUENCE: 66

Met Glu Leu Thr Met Leu Asp Tyr Asp Met Val His Phe Pro Pro
1               5                   10                  15

<210> SEQ ID NO 67
<211> LENGTH: 15
<212> TYPE: PRT
<213> ORGANISM: Artificial sequence

```
<220> FEATURE:
<223> OTHER INFORMATION: synthetic peptide CCNB1 332-346

<400> SEQUENCE: 67

Leu Asp Tyr Asp Met Val His Phe Pro Pro Ser Gln Ile Ala Ala
1               5                   10                  15

<210> SEQ ID NO 68
<211> LENGTH: 15
<212> TYPE: PRT
<213> ORGANISM: Artificial sequence
<220> FEATURE:
<223> OTHER INFORMATION: synthetic peptide CCNB1 338-352

<400> SEQUENCE: 68

His Phe Pro Pro Ser Gln Ile Ala Ala Gly Ala Phe Cys Leu Ala
1               5                   10                  15

<210> SEQ ID NO 69
<211> LENGTH: 15
<212> TYPE: PRT
<213> ORGANISM: Artificial sequence
<220> FEATURE:
<223> OTHER INFORMATION: synthetic peptide CCNB1 342-356

<400> SEQUENCE: 69

Ser Gln Ile Ala Ala Gly Ala Phe Cys Leu Ala Leu Lys Ile Leu
1               5                   10                  15

<210> SEQ ID NO 70
<211> LENGTH: 15
<212> TYPE: PRT
<213> ORGANISM: Artificial sequence
<220> FEATURE:
<223> OTHER INFORMATION: synthetic peptide CCNB1 347-361

<400> SEQUENCE: 70

Gly Ala Phe Cys Leu Ala Leu Lys Ile Leu Asp Asn Gly Glu Trp
1               5                   10                  15

<210> SEQ ID NO 71
<211> LENGTH: 15
<212> TYPE: PRT
<213> ORGANISM: Artificial sequence
<220> FEATURE:
<223> OTHER INFORMATION: synthetic peptide CCNB1 351-365

<400> SEQUENCE: 71

Leu Ala Leu Lys Ile Leu Asp Asn Gly Glu Trp Thr Pro Thr Leu
1               5                   10                  15

<210> SEQ ID NO 72
<211> LENGTH: 15
<212> TYPE: PRT
<213> ORGANISM: Artificial sequence
<220> FEATURE:
<223> OTHER INFORMATION: synthetic peptide CCNB1 359-373

<400> SEQUENCE: 72

Gly Glu Trp Thr Pro Thr Leu Gln His Tyr Leu Ser Tyr Thr Glu
1               5                   10                  15

<210> SEQ ID NO 73
<211> LENGTH: 15
<212> TYPE: PRT
<213> ORGANISM: Artificial sequence
<220> FEATURE:
```

-continued

<223> OTHER INFORMATION: synthetic peptide CCNB1 363-377

<400> SEQUENCE: 73

Pro Thr Leu Gln His Tyr Leu Ser Tyr Thr Glu Glu Ser Leu Leu
1               5                   10                  15

<210> SEQ ID NO 74
<211> LENGTH: 15
<212> TYPE: PRT
<213> ORGANISM: Artificial sequence
<220> FEATURE:
<223> OTHER INFORMATION: synthetic peptide CCNB1 366-380

<400> SEQUENCE: 74

Gln His Tyr Leu Ser Tyr Thr Glu Glu Ser Leu Leu Pro Val Met
1               5                   10                  15

<210> SEQ ID NO 75
<211> LENGTH: 15
<212> TYPE: PRT
<213> ORGANISM: Artificial sequence
<220> FEATURE:
<223> OTHER INFORMATION: synthetic peptide CCNB1 369-383

<400> SEQUENCE: 75

Leu Ser Tyr Thr Glu Glu Ser Leu Leu Pro Val Met Gln His Leu
1               5                   10                  15

<210> SEQ ID NO 76
<211> LENGTH: 15
<212> TYPE: PRT
<213> ORGANISM: Artificial sequence
<220> FEATURE:
<223> OTHER INFORMATION: synthetic peptide CCNB1 374-388

<400> SEQUENCE: 76

Glu Ser Leu Leu Pro Val Met Gln His Leu Ala Lys Asn Val Val
1               5                   10                  15

<210> SEQ ID NO 77
<211> LENGTH: 15
<212> TYPE: PRT
<213> ORGANISM: Artificial sequence
<220> FEATURE:
<223> OTHER INFORMATION: synthetic peptide CCNB1 377-391

<400> SEQUENCE: 77

Leu Pro Val Met Gln His Leu Ala Lys Asn Val Val Met Val Asn
1               5                   10                  15

<210> SEQ ID NO 78
<211> LENGTH: 15
<212> TYPE: PRT
<213> ORGANISM: Artificial sequence
<220> FEATURE:
<223> OTHER INFORMATION: synthetic peptide CCNB1 385-399

<400> SEQUENCE: 78

Lys Asn Val Val Met Val Asn Gln Gly Leu Thr Lys His Met Thr
1               5                   10                  15

<210> SEQ ID NO 79
<211> LENGTH: 15
<212> TYPE: PRT
<213> ORGANISM: Artificial sequence
<220> FEATURE:
<223> OTHER INFORMATION: synthetic peptide CCNB1 392-406

<400> SEQUENCE: 79

Gln Gly Leu Thr Lys His Met Thr Val Lys Asn Lys Tyr Ala Thr
1               5                   10                  15

<210> SEQ ID NO 80
<211> LENGTH: 15
<212> TYPE: PRT
<213> ORGANISM: Artificial sequence
<220> FEATURE:
<223> OTHER INFORMATION: synthetic peptide CCNB1 396-410

<400> SEQUENCE: 80

Lys His Met Thr Val Lys Asn Lys Tyr Ala Thr Ser Lys His Ala
1               5                   10                  15

<210> SEQ ID NO 81
<211> LENGTH: 15
<212> TYPE: PRT
<213> ORGANISM: Artificial sequence
<220> FEATURE:
<223> OTHER INFORMATION: synthetic peptide CCNB1 402-416

<400> SEQUENCE: 81

Asn Lys Tyr Ala Thr Ser Lys His Ala Lys Ile Ser Thr Leu Pro
1               5                   10                  15

<210> SEQ ID NO 82
<211> LENGTH: 15
<212> TYPE: PRT
<213> ORGANISM: Artificial sequence
<220> FEATURE:
<223> OTHER INFORMATION: synthetic peptide CCNB1 410-424

<400> SEQUENCE: 82

Ala Lys Ile Ser Thr Leu Pro Gln Leu Asn Ser Ala Leu Val Gln
1               5                   10                  15

<210> SEQ ID NO 83
<211> LENGTH: 15
<212> TYPE: PRT
<213> ORGANISM: Artificial sequence
<220> FEATURE:
<223> OTHER INFORMATION: synthetic peptide CCNB1 416-430

<400> SEQUENCE: 83

Pro Gln Leu Asn Ser Ala Leu Val Gln Asp Leu Ala Lys Ala Val
1               5                   10                  15

<210> SEQ ID NO 84
<211> LENGTH: 15
<212> TYPE: PRT
<213> ORGANISM: Artificial sequence
<220> FEATURE:
<223> OTHER INFORMATION: synthetic peptide CCNB1 419-433

<400> SEQUENCE: 84

Asn Ser Ala Leu Val Gln Asp Leu Ala Lys Ala Val Ala Lys Val
1               5                   10                  15

<210> SEQ ID NO 85
<211> LENGTH: 18
<212> TYPE: PRT
<213> ORGANISM: Artificial sequence
<220> FEATURE:
<223> OTHER INFORMATION: synthetic peptide CCNB1 199-216

```
<400> SEQUENCE: 85

Gly Asn Met Arg Ala Ile Leu Ile Asp Trp Leu Val Gln Val Gln Met
1               5                   10                  15

Lys Phe

<210> SEQ ID NO 86
<211> LENGTH: 18
<212> TYPE: PRT
<213> ORGANISM: Artificial sequence
<220> FEATURE:
<223> OTHER INFORMATION: synthetic peptide CCNB1 241-258

<400> SEQUENCE: 86

Lys Lys Met Leu Gln Leu Val Gly Val Thr Ala Met Phe Ile Ala Ser
1               5                   10                  15

Lys Tyr

<210> SEQ ID NO 87
<211> LENGTH: 20
<212> TYPE: PRT
<213> ORGANISM: Artificial sequence
<220> FEATURE:
<223> OTHER INFORMATION: synthetic peptide CCNB1 280-299

<400> SEQUENCE: 87

His Gln Ile Arg Gln Met Glu Met Lys Ile Leu Arg Ala Leu Asn Phe
1               5                   10                  15

Gly Leu Gly Arg
            20

<210> SEQ ID NO 88
<211> LENGTH: 19
<212> TYPE: PRT
<213> ORGANISM: Artificial sequence
<220> FEATURE:
<223> OTHER INFORMATION: synthetic peptide CCNB1 299-317

<400> SEQUENCE: 88

Arg Pro Leu Pro Leu His Phe Leu Arg Arg Ala Ser Lys Ile Gly Glu
1               5                   10                  15

Val Asp Val

<210> SEQ ID NO 89
<211> LENGTH: 18
<212> TYPE: PRT
<213> ORGANISM: Artificial sequence
<220> FEATURE:
<223> OTHER INFORMATION: synthetic peptide CCNB1 320-337

<400> SEQUENCE: 89

His Thr Leu Ala Lys Tyr Leu Met Glu Leu Thr Met Leu Asp Tyr Asp
1               5                   10                  15

Met Val

<210> SEQ ID NO 90
<211> LENGTH: 18
<212> TYPE: PRT
<213> ORGANISM: Artificial sequence
<220> FEATURE:
<223> OTHER INFORMATION: synthetic peptide CCNB1 363-380

<400> SEQUENCE: 90

Pro Thr Leu Gln His Tyr Leu Ser Tyr Thr Glu Glu Ser Leu Leu Pro
```

```
1               5                   10                  15

Val Met

<210> SEQ ID NO 91
<211> LENGTH: 18
<212> TYPE: PRT
<213> ORGANISM: Artificial sequence
<220> FEATURE:
<223> OTHER INFORMATION: synthetic peptide CCNB1 416-433

<400> SEQUENCE: 91

Pro Gln Leu Asn Ser Ala Leu Val Gln Asp Leu Ala Lys Ala Val Ala
1               5                   10                  15

Lys Val

<210> SEQ ID NO 92
<211> LENGTH: 9
<212> TYPE: PRT
<213> ORGANISM: Artificial sequence
<220> FEATURE:
<223> OTHER INFORMATION: synthetic peptide survivine 96-104

<400> SEQUENCE: 92

Leu Thr Leu Gly Glu Phe Leu Lys Leu
1               5

<210> SEQ ID NO 93
<211> LENGTH: 10
<212> TYPE: PRT
<213> ORGANISM: Artificial sequence
<220> FEATURE:
<223> OTHER INFORMATION: synthetic peptide survivine 95-104

<400> SEQUENCE: 93

Glu Leu Thr Leu Gly Glu Phe Leu Lys Leu
1               5                   10

<210> SEQ ID NO 94
<211> LENGTH: 9
<212> TYPE: PRT
<213> ORGANISM: Artificial sequence
<220> FEATURE:
<223> OTHER INFORMATION: synthetic peptide survivine-2B 80-88

<400> SEQUENCE: 94

Ala Tyr Ala Cys Asn Thr Ser Thr Leu
1               5

<210> SEQ ID NO 95
<211> LENGTH: 11
<212> TYPE: PRT
<213> ORGANISM: Artificial sequence
<220> FEATURE:
<223> OTHER INFORMATION: synthetic peptide PADRE
<220> FEATURE:
<221> NAME/KEY: misc_feature
<222> LOCATION: (2)..(2)
<223> OTHER INFORMATION: Xaa can be any naturally occurring amino acid

<400> SEQUENCE: 95

Lys Xaa Val Ala Ala Trp Thr Leu Lys Ala Ala
1               5                   10

<210> SEQ ID NO 96
<211> LENGTH: 9
<212> TYPE: PRT
```

<213> ORGANISM: Artificial sequence
<220> FEATURE:
<223> OTHER INFORMATION: synthetic peptide P1

<400> SEQUENCE: 96

Ala Gly Tyr Leu Met Glu Leu Cys Val
1               5

<210> SEQ ID NO 97
<211> LENGTH: 9
<212> TYPE: PRT
<213> ORGANISM: Artificial sequence
<220> FEATURE:
<223> OTHER INFORMATION: synthetic peptide P2

<400> SEQUENCE: 97

Ala Gly Tyr Leu Met Glu Leu Cys Met
1               5

<210> SEQ ID NO 98
<211> LENGTH: 9
<212> TYPE: PRT
<213> ORGANISM: Artificial sequence
<220> FEATURE:
<223> OTHER INFORMATION: synthetic peptide P3

<400> SEQUENCE: 98

Ala Gly Tyr Leu Met Glu Leu Cys Phe
1               5

<210> SEQ ID NO 99
<211> LENGTH: 9
<212> TYPE: PRT
<213> ORGANISM: Artificial sequence
<220> FEATURE:
<223> OTHER INFORMATION: synthetic peptide P4

<400> SEQUENCE: 99

Ala Gly Tyr Leu Met Glu Leu Cys Cys
1               5

<210> SEQ ID NO 100
<211> LENGTH: 10
<212> TYPE: PRT
<213> ORGANISM: Artificial sequence
<220> FEATURE:
<223> OTHER INFORMATION: synthetic peptide P5

<400> SEQUENCE: 100

Ala Gly Tyr Leu Met Glu Leu Cys Met Ala
1               5                   10

<210> SEQ ID NO 101
<211> LENGTH: 10
<212> TYPE: PRT
<213> ORGANISM: Artificial sequence
<220> FEATURE:
<223> OTHER INFORMATION: synthetic peptide P6

<400> SEQUENCE: 101

Ala Gly Tyr Leu Met Glu Leu Cys Phe Ala
1               5                   10

<210> SEQ ID NO 102
<211> LENGTH: 9
<212> TYPE: PRT
<213> ORGANISM: Artificial sequence -continued

```
<220> FEATURE:
<223> OTHER INFORMATION: synthetic peptide CB9

<400> SEQUENCE: 102

Ala Lys Tyr Leu Met Glu Leu Thr Met
1               5

<210> SEQ ID NO 103
<211> LENGTH: 10
<212> TYPE: PRT
<213> ORGANISM: Artificial sequence
<220> FEATURE:
<223> OTHER INFORMATION: synthetic peptide CB10

<400> SEQUENCE: 103

Ala Lys Tyr Leu Met Glu Leu Thr Met Leu
1               5                   10

<210> SEQ ID NO 104
<211> LENGTH: 9
<212> TYPE: PRT
<213> ORGANISM: Artificial sequence
<220> FEATURE:
<223> OTHER INFORMATION: synthetic peptide CB9L2

<400> SEQUENCE: 104

Ala Leu Tyr Leu Met Glu Leu Thr Met
1               5

<210> SEQ ID NO 105
<211> LENGTH: 9
<212> TYPE: PRT
<213> ORGANISM: Artificial sequence
<220> FEATURE:
<223> OTHER INFORMATION: synthetic peptide CB9M2

<400> SEQUENCE: 105

Ala Met Tyr Leu Met Glu Leu Thr Met
1               5

<210> SEQ ID NO 106
<211> LENGTH: 9
<212> TYPE: PRT
<213> ORGANISM: Artificial sequence
<220> FEATURE:
<223> OTHER INFORMATION: synthetic peptide CB204

<400> SEQUENCE: 106

Ile Leu Ile Asp Trp Leu Val Gln Val
1               5

<210> SEQ ID NO 107
<211> LENGTH: 15
<212> TYPE: PRT
<213> ORGANISM: Artificial sequence
<220> FEATURE:
<223> OTHER INFORMATION: synthetic peptide CB215-229

<400> SEQUENCE: 107

Lys Phe Arg Leu Leu Gln Glu Thr Met Tyr Met Thr Val Ser Ile
1               5                   10                  15

<210> SEQ ID NO 108
<211> LENGTH: 15
<212> TYPE: PRT
<213> ORGANISM: Artificial sequence
<220> FEATURE:
```

```
<223> OTHER INFORMATION: synthetic peptide CB219-233

<400> SEQUENCE: 108

Leu Gln Glu Thr Met Tyr Met Thr Val Ser Ile Ile Asp Arg Phe
1               5                   10                  15

<210> SEQ ID NO 109
<211> LENGTH: 12
<212> TYPE: PRT
<213> ORGANISM: Artificial sequence
<220> FEATURE:
<223> OTHER INFORMATION: synthetic peptide CB223-234

<400> SEQUENCE: 109

Met Tyr Met Thr Val Ser Ile Ile Asp Arg Phe Met
1               5                   10
```